United States Patent [19]

Piwinski et al.

[11] Patent Number: 5,432,175

[45] Date of Patent: Jul. 11, 1995

[54] PYRIDINE AND PYRIDINE N-OXIDE DERIVATIVES OF DIARYL METHYL PIPERIDINES OR PIPERAZINES, AND COMPOSITIONS AND METHODS OF USE THEREOF

[75] Inventors: John J. Piwinski, Parsippany; Jesse Wong, Union; Michael J. Green, Skillman; Vera Seidl, Wayne; Richard Friary, West Orange, all of N.J.

[73] Assignee: Schering Corporation, Kenilworth, N.J.

[21] Appl. No.: 30,454

[22] PCT Filed: Oct. 8, 1991

[86] PCT No.: PCT/US91/07169

§ 371 Date: Apr. 1, 1993

§ 102(e) Date: Apr. 1, 1993

[87] PCT Pub. No.: WO92/06971

PCT Pub. Date: Apr. 30, 1992

Related U.S. Application Data

[63] Continuation-in-part of Ser. No. 595,330, Oct. 10, 1990, abandoned.

[51] Int. Cl.⁶ ............... A61K 31/495; A61K 31/445; C07D 401/06; C07D 417/06
[52] U.S. Cl. ................... 514/252; 514/255; 514/318; 514/326; 514/360; 514/364; 514/369; 546/193; 546/194; 546/209; 546/210; 546/212; 546/225; 546/241; 546/243; 548/200
[58] Field of Search ............... 544/360, 364; 514/252, 514/255, 318, 326; 546/193, 194

[56] References Cited

U.S. PATENT DOCUMENTS

| | | | |
|---|---|---|---|
| 2,739,968 | 3/1956 | Sperber | 514/330 |
| 2,898,339 | 8/1959 | Wheeler et al. | 514/317 |
| 3,922,276 | 11/1973 | Duncan, Jr. et al. | 544/129 |
| 3,956,296 | 5/1976 | Duncan | 514/330 |
| 4,032,642 | 6/1977 | Duncan, Jr. et al. | 514/330 |
| 4,105,849 | 8/1978 | Hamilton et al. | 544/129 |
| 4,540,780 | 9/1985 | Downs et al. | 544/129 |
| 4,591,590 | 5/1986 | Ueda et al. | 514/252 |
| 4,632,925 | 12/1986 | Mullin et al. | 514/256 |
| 4,797,489 | 1/1989 | Abou-Gharbia et al. | 544/331 |
| 4,826,853 | 5/1989 | Piwinski et al. | 514/290 |
| 4,835,157 | 5/1989 | Press et al. | 514/258 |
| 5,089,496 | 2/1992 | Piwinski et al. | 544/361 |
| 5,104,876 | 4/1992 | Piwinski et al. | 544/361 |
| 5,151,423 | 9/1992 | Piwinski et al. | 544/361 |
| 5,166,205 | 11/1992 | Cuberes-Altisent et al. | 514/252 |

FOREIGN PATENT DOCUMENTS

| | | |
|---|---|---|
| 0113226 | 7/1984 | European Pat. Off. |
| 0235463 | 9/1987 | European Pat. Off. |
| 0283310 | 9/1988 | European Pat. Off. |
| 864458 | 6/1986 | South Africa |
| 864522 | 6/1986 | South Africa |
| 91/10647 | 7/1991 | WIPO |

OTHER PUBLICATIONS

Cid et al. Tetrahedron, vol. 44, No. 19, pp. 6197 to 6200 (1988).
Meyer et al., Journal of Medicinal Chemistry 1989, vol. 32, No. 3 pp. 593–597.
Ohtaka et al, Chem Pharm. Bull. 35 (10) 4124–4129 (1987).
Kennis et al., Drug Development Research 8: 133–140 (1986).
Regnier et al., Eur. J. Med Chem. 22 (1987) 243–250.
Nishikawa et al., J. Med. Chem. 1989, 32, 583–593.
Anagnostopulos et al., Eur. J. Med. Chem. 24 (1989) 227–232.
Ohtaka et al., Chem. Pharm. Bull. 35 (8) 3270–3275 (1987).

*Primary Examiner*—Cecilia Tsang
*Attorney, Agent, or Firm*—Henry C. Jeanette; James R. Nelson

[57] ABSTRACT

Pyridine and pyridine N-oxide derivatives of diaryl methyl piperidines or piperazines and pharmaceutically acceptable salts thereof are disclosed, which possess anti-allergic and anti-inflammatory activity. Pharmaceutical compositions containing and methods of using the compounds are also described.

17 Claims, No Drawings

PYRIDINE AND PYRIDINE N-OXIDE DERIVATIVES OF DIARYL METHYL PIPERIDINES OR PIPERAZINES, AND COMPOSITIONS AND METHODS OF USE THEREOF

This application is the 371 application of PCT/US 91/07169, filed Oct. 8, 1991, which is in turn a continuation-in-part of U.S. Ser. No. 07/595,330, filed Oct. 10, 1990, now abandoned.

BACKGROUND OF THE INVENTION

The present invention relates to pyridine and pyridine N-oxide derivatives of diaryl methyl piperidines or piperazines and to pharmaceutical compositions and methods of using such compounds.

European Patent Application No. 0 113 226 discloses benzhydrylpiperazine derivatives of the formula:

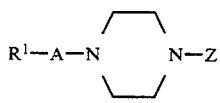

wherein

A is lower alkylene,

Z is benzhydryl optionally substituted with halogen, and $R^1$ is amino, aryl, pyridyl, acyl or acylamino, in which the aryl group and pyridyl group are substituted with nitro, amino or acylamino, provided that Z is benzhydryl substituted with halogen, when $R^1$ is amino, and pharmaceutically acceptable salts thereof. These compounds are said to possess anti-allergic activities. Other similar piperazine compounds are disclosed in South African published Patent Application Nos. 864522 and 864458 and in European Patent Application No. 0 283 310.

SUMMARY OF THE INVENTION

We have now unexpectedly found that compounds represented by the structural formula 1.0 below have good activity as PAF antagonists and antihistamines:

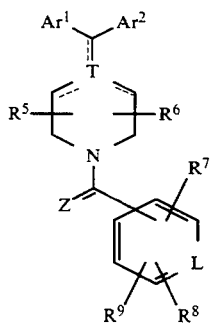

or a pharmaceutically acceptable salt or solvate thereof, wherein:

$Ar^1$ represents

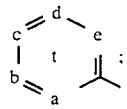

$Ar^2$ represents

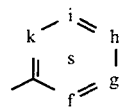

or a five-membered heterocyclic aromatic group containing at least one

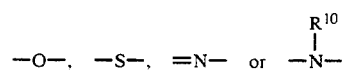

in the ring structure, wherein the substitutable carbon atoms of the five-membered heterocyclic group may optionally be substituted with a group $R^1$ as defined below;

one of a, b, c, d and e represents N or NO and the others represent CH or $CR^1$ or all of a, b, c, d and e represent CH or $CR^1$;

one of f, g, h, i and k represents N or NO and the others represent CH or $CR^2$ or all of f, g, h, i and k represent CH or $CR^2$;

L represents N or $N^+O^-$;

$R^1$ and $R^2$ may be the same or different and each $R^1$ and each $R^2$ independently represents halo, $-CF_3$, $-OR^{11}$, $-C(O)R^{11}$, $-SR^{11}$, $-S(O)_eR^{12}$ where e is 1 or 2, $-N(R^{11})_2$, $-NO_2$, $-OC(O)R^{11}$, $-CO_2R^{11}$, $-OCO_2R^{12}$, $-CON(R^{11})_2$, $-NR^{11}C(=O)R^{11}$, $-CN$, alkyl, aryl, alkenyl or alkynyl, which alkyl group may be substituted with $-OR^{11}$, $-SR^{11}$, $-N(R^{11})_2$ or $-CO_2R^{11}$ and which alkenyl group may be substituted with halo, $-OR^{12}$ or $-CO_2R^{11}$;

in addition, two adjacent $R^1$ groups on ring t may together form a benzene ring fused to the ring t and/or two adjacent $R^2$ groups on ring s may together form a benzene ring fused to the ring s;

$R^5$ and $R^6$ may be the same or different and each independently represents H, alkyl or aryl, which alkyl may be substituted with $-OR^{11}$, $-SR^{11}$ or $-N(R^{11})_2$;

in addition, $R^5$ and $R^6$ together on the same carbon atom may represent $=O$ or $=S$;

each of R70 $R^8$ and R9 independently represents H, halo, $-CF_3$, $-OR^{11}$, $-C(O)R^{11}$, $SR^{11}$, $-S(O)_eR^{12}$ where e is 1 or 2, $-N(R^{11})_2$, $-NO_2$, $-CN$, $-CO_2R^{11}$, $-OCO_2R^{12}$, $-OC(O)R^{11}$, $-CON(R^{11})_2$, $-NR^{11}C(O)R^{11}$, alkyl, aryl, alkenyl or alkynyl, which alkyl group may be substituted with $-OR^{11}$, $-SR^{11}$, $-N(R^{11})_2$, or $-CO_2R11$ and which alkenyl group may be substituted with halo, $-OR^{12}$ or $-CO_2R^{11}$;

$R^{10}$ represents H or alkyl;

each $R^{11}$ independently represents H, alkyl or aryl;

each $R^{12}$ independently represents alkyl or aryl;

T represents CH, C or N, with the dotted lines attached to T representing one double bond in one of the indicated positions when T is C and being absent when T is CH or N; and Z represents O or S, or Z may optionally represent H and $R^{10}$ when (a) L represents $N^+O^-$, or (b) $Ar^2$ represents a five-membered heterocyclic aromatic group, or (c) T represents C or CH.

In a preferred embodiment of the invention, the compound of the invention is of the formula 1.1:

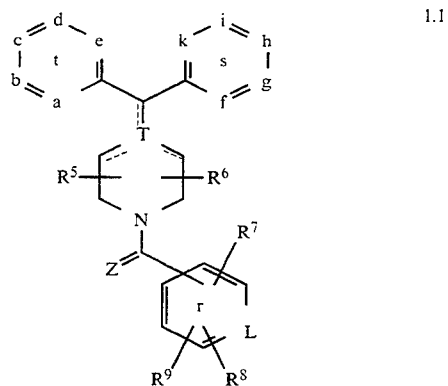

1.1 where a, b, c, d, e, f, g, h, i, k, T, Z, L, $R^5$, $R^6$, $R^7$, $R^8$ and $R^9$ are as defined above. Preferably, a, b, c,d and e each independently represent CH or $CR^1$, and f, g h, i and k each independently represent CH or $CR^2$. In an alternative preferred embodiment, one of a, b, c, d, e, f, g, h, i and k represents N or NO and each of the others independently represents CH or $CR^1$ in the case of ring t or CH or $CR^2$ in the case of ring s. Preferably, a represents N or NO and each of b, c, d, e, f, g, h, i and k independently represents CH or $CR^1$ in the case of ring t or CH or $CR^2$ in the case of ring s. Z preferably represents O. Alternatively, Z preferably represents two atoms of hydrogen when L represents $N^+O^-$ or when T represents C or CH (preferably C). When present, each $R^1$ and each $R^2$ preferably independently represent alkyl, halo, $N(R^{11})_2$ or $OR^{11}$. $R^5$ and $R^6$ preferably each independently represent H or alkyl. $R^8$ and $R^9$ preferably are both H. $R^7$ preferably represents H, halo, —$CF_3$, —$OR^{11}$, —SR11, —$N(R^{11})_2$ or alkyl. L is preferably in the para position relative to the bond connecting the pyridine ring r to the rest of the compound and is more preferably $N^+O^-$.

In a particularly preferred embodiment, the compounds of the invention are represented by the structural formula 1.2:

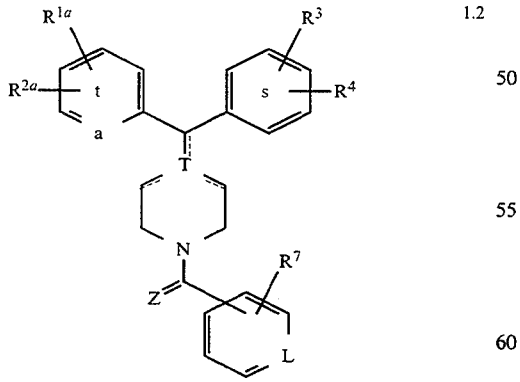

1.2 or a pharmaceutically acceptable salt or solvate thereof, wherein:
a represents CH, N or $N^+O^-$;
L represents N or $N^+O^-$;
$R^{1a}$, $R^{2a}$, $R^3$, $R^4$ and $R^7$ represent optional substituents which may be the same or different and each independently represents halo, —$CF_3$, —$OR^{11}$, $SR^{11}$, —$N(R^{11})_2$, alkyl, alkenyl or alkynyl;

$R^{11}$ represents H, alkyl or aryl;

T represents CH, C or N, with the dotted line attached to T representing a double bond when T is C and being absent when T is CH or N; and Z represents O or S, or Z may optionally represent H and $R^{10}$ when either (a) L represents $N^+O^-$ or (b) T represents C or CH.

In this formula 1.2, L preferably represents $N^+O^-$. T preferably represents N and the optional double bond to T is absent. Alternatively, T represents C and the optional double bond to T is present. $R^1$ and $R^2$ preferably are absent, i.e., b, c, d and e represent CH. When present, $R^3$ and $R^4$ preferably each independently represent halo. $R^7$ preferably represents H. Z preferably represents O and L is preferably in the para position relative to the bond connecting the pyridine ring to the rest of the compound.

Other preferred embodiments of the invention include compounds of the formulas:

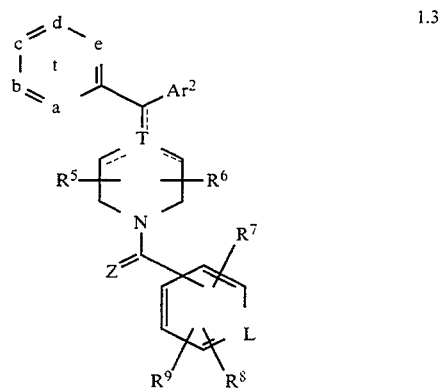

1.3

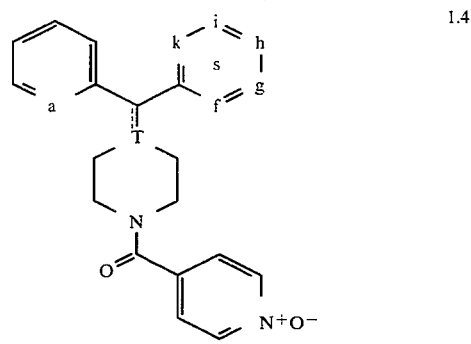

1.4

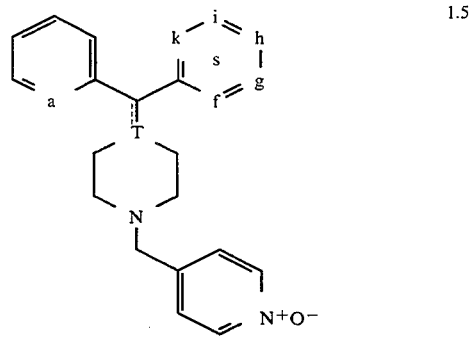

1.5

-continued

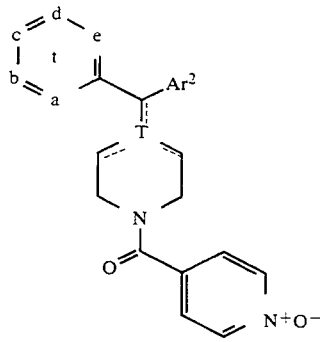

and

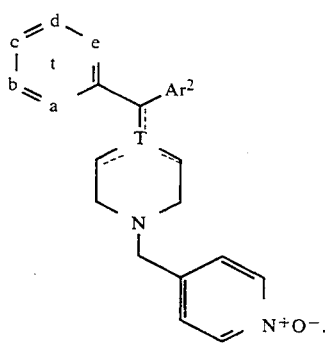

In formula 1.3, a, b, c, d, e, T, Z, L, $R^5$, $R^6$, $R^7$, $R^8$ and $R^9$ are as defined above and $Ar^2$ represents a five-membered heterocyclic group selected from:

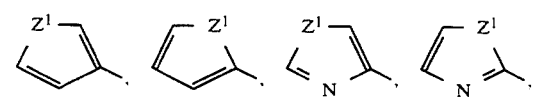

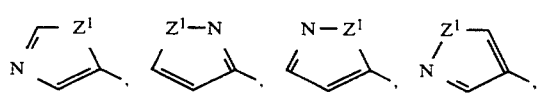

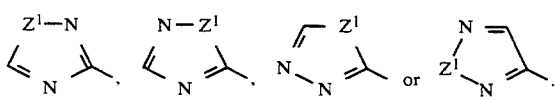

where $Z^1$ represents

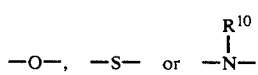

and $R^{10}$ is defined as above. In formula 1.4, f, g, h, i, k and T are as defined above and a is N or CH. In formula 1.5, f, g, h, i, k and T are as defined above and a is N or CH. In formula 1.6, a, b, c, d, e and T are as defined above and $Ar^2$ is selected from:

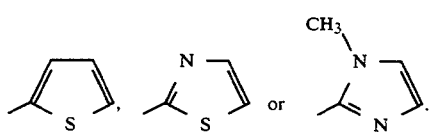

In formula 1.7, a, b, c, d, e and T are as defined above and $Ar^2$ is selected from:

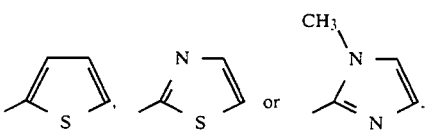

In the above formulas 1.2, 1.3, 1.4, 1.5, 1.6 and 1.7, the following terms have the indicated meanings when employed: each $R^1$ and each $R^2$ preferably independently represent alkyl, halo, $N(R^{11})_2$, $-CF_3$, $-SR^{11}$ or $OR^{11}$; $R^5$ and $R^6$ preferably each independently represent H or alkyl; $R^8$ and $R^9$ preferably are both H; and $R^7$ preferably represents H, halo, $-CF_3$, $-OR^{11}$, $-SR^{11}$, $-N(R^{11})_2$ or alkyl.

Preferred compounds of the invention include:

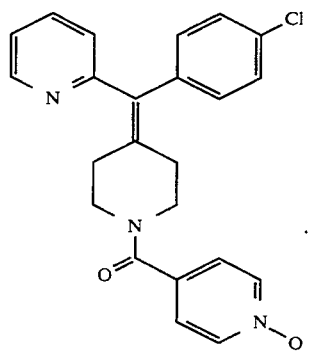

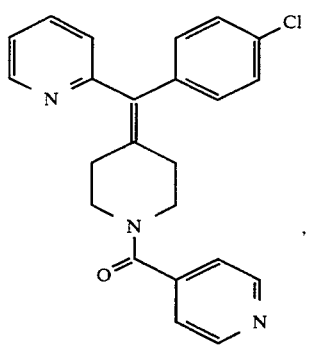

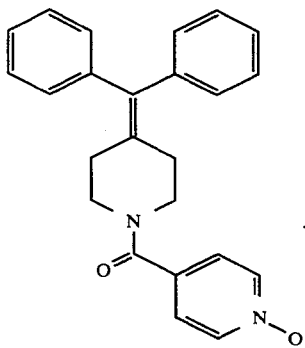

-continued
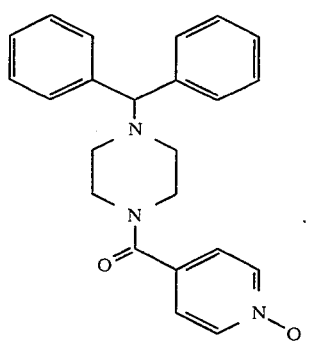
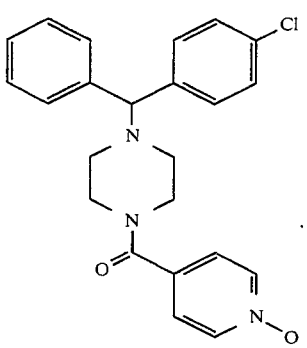
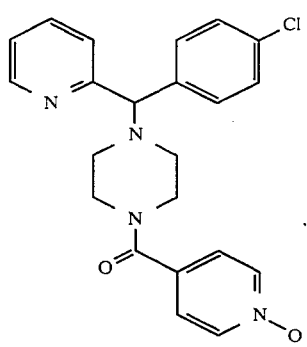
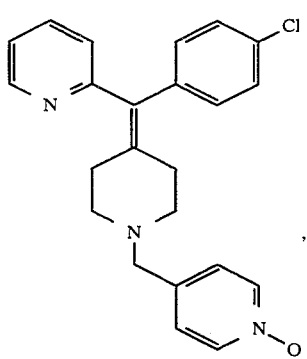
-continued
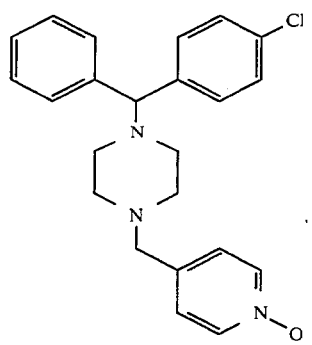
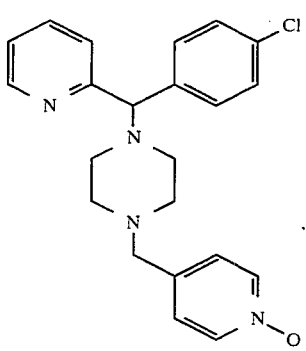
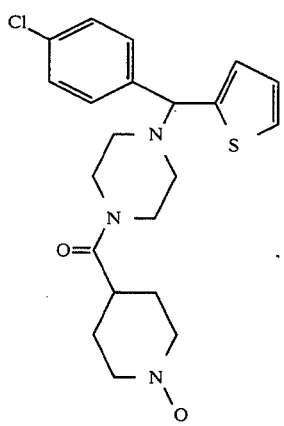
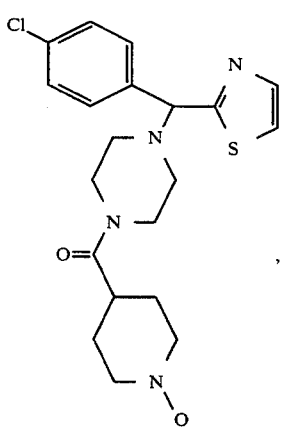

-continued
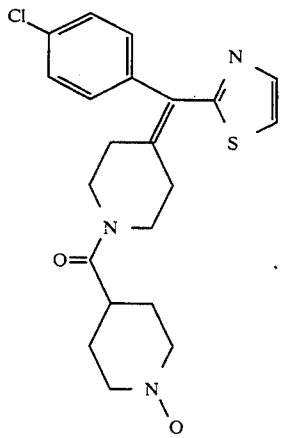
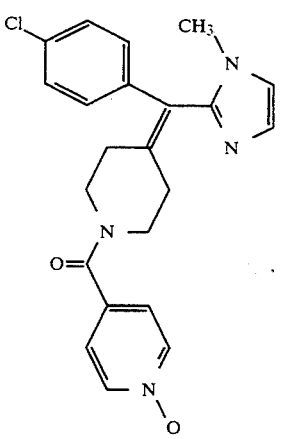
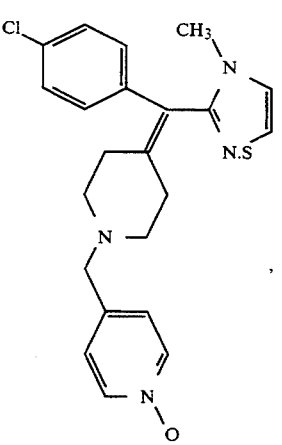
-continued
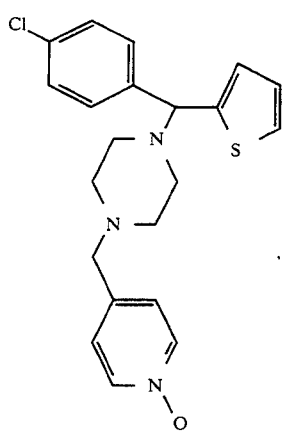
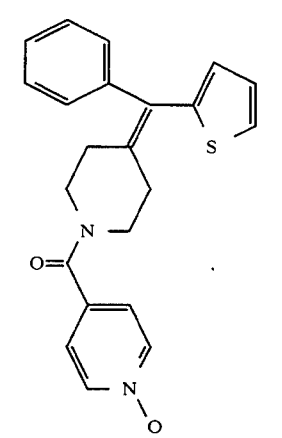
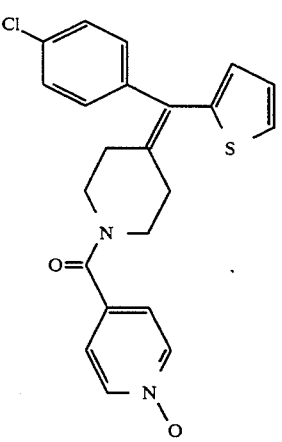

-continued

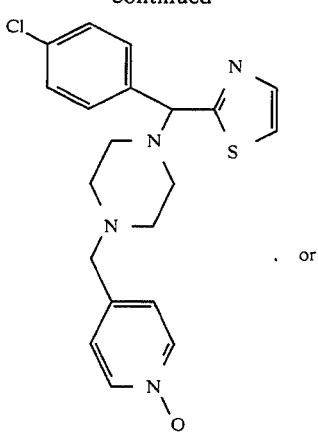

, or

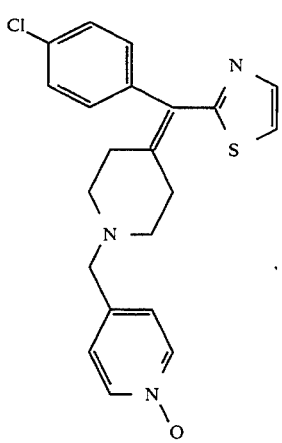

or a pharmaceutically acceptable salt of such a compound.

The invention also involves a pharmaceutical composition comprising a compound of formula 1.0 above in combination with a pharmaceutically acceptable carrier and methods of treating allergic reactions and/or inflammation in a mammal by administering to the mammal an antiallergic or antiinflammatory effective amount of a compound of formula 1.0, i.e., the use of a compound of formula 1.0 for the manufacture of a medicament for the treatment of allergic reaction or inflammation.

DETAILED DESCRIPTION OF THE INVENTION

Certain compounds of the invention may exist in different isomeric (e.g., enantiomers and diastereoisomers) as well as conformational forms. The invention contemplates all such isomers both in pure form and in admixture, including racemic mixtures. Enol and tautomeric forms are also included. For example, hydroxy substituted pyridinyl groups can also exists in their keto form:

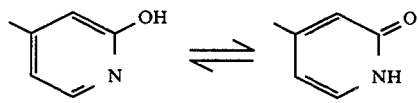

as can certain members of the five-membered heterocyclic groups.

The compounds of the invention of formula 1.0 can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

When T represents C, the compounds of formula 1.0 have one double bond in one of the indicated positions, i.e.,

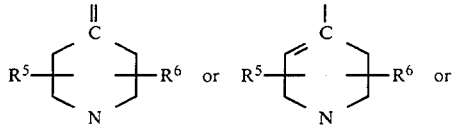

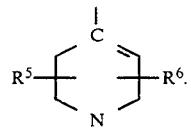

The position of the double bond depends on the substituents $R^5$ and $R^6$, but usually the double bond is external to the piperidine ring.

As noted above, the $Ar^1$ and $Ar^2$ groups of formulas 1.0-1.7 may contain one or more substituents $R^1$, $R^{1a}$, $R^2$, $R^{2a}$, $R^3$ and $R^4$ where indicated. In compounds where there is more than one such substituent, each substituent on the ring may be the same or different. Thus, compounds having combinations of such substituents are within the scope of the invention. Also, the lines drawn into the rings from the $R^1$-$R^9$ groups indicate that such groups may be attached at any of the available positions. For example, the $R^{1a}$ and $R^{2a}$ groups may be attached to any carbon atom in ring t of formula 1.2, while the $R^3$ and $R^4$ groups may be attached to any carbon atom of rings of formula 1.2.

$R^5$ and $R^6$ are attached to the piperidyl, piperidinylidenyl or piperazinyl ring. As such they may be the same or different. The variables $R^5$ and $R^6$ in addition to representing H, may represent variables attached to the same or different carbon atoms in said ring. For example, when $R^5$ and $R^6$ are combined to represent =O or =S, they are attached to the same carbon atom.

The N-oxides are illustrated herein using the terms NO, N→O, N-O and N⁺O⁻. All are considered equivalent as used herein.

Lines drawn into the ring systems indicate that the indicated bond may be attached to any of the substitutable ring carbon atoms.

Certain compounds of the invention will be acidic in nature, e.g. those compounds which possess a carboxyl, phenolic enolic or tautomeric hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

As used herein, the following terms are used as defined below unless otherwise indicated:

alkyl—(including the alkyl portions of alkoxy, alkylamino and dialkylamino)—represents straight and branched carbon chains and contains from one to twenty carbon atoms, preferably one to six carbon atoms;

cycloalkyl—represents saturated carbocyclic rings of from 3 to 20 carbon atoms, preferably 3 to 7 carbon atoms;

alkenyl—represents straight and branched carbon chains having at least one carbon to carbon double bond and containing from 2 to 12 carbon atoms, preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_p$R$^a$ [wherein p is 0, 1 or 2 and R$^a$ is alkyl, phenyl or substituted phenyl], —CF$_3$, amino, alkylamino, dialkylamino, —COOR$^{10}$ or —NO$_2$;

substituted phenyl—represents a phenyl group in which 1 to 3 hydrogen atoms thereof are replaced by the same or different substituents independently chosen from halo, alkyl, hydroxy, alkoxy, phenoxy, cyano, cycloalkyl, alkenyloxy, alkynyloxy, —SH, —S(O)$_p$R$^a$ [wherein p is 0, 1 or 2 and R$^a$ is alkyl], —CF$_3$, amino, alkylamino, dialkylamino, —COOR$^{10}$ or —NO$_2$;

five-membered heterocyclic aromatic group—represents a carbocyclic group having two double bonds (either —N=CH—, —N=N— or —CH=CH—) and at least one —O—, —S—, —N= and/or

interrupting the carbocyclic ring structure, in which all available substitutable carbon atoms of the heterocyclic aromatic group are intended as possible points of attachment, and preferably the five-membered heterocyclic aromatic group is selected from those groups specifically listed above; and halo—represents fluoro, chloro, bromo and iodo.

The following processes A–H below may be employed to produce compounds of general structural formula 1.0.

A. A compound of general formula 2.0 can be coupled with a compound of the formula 3.0 in the presence of coupling agent such as 1-(3-dimethylaminopropyl)-3-ethyl carbodiimide hydrochloride (DEC), N,N'-dicyclohexylcarbodiimide (DCC) or N,N'-carbonyldiimidazole (CDI) to produce compounds of general structural 1.0 where Z is oxygen (i.e., formula 1.8):

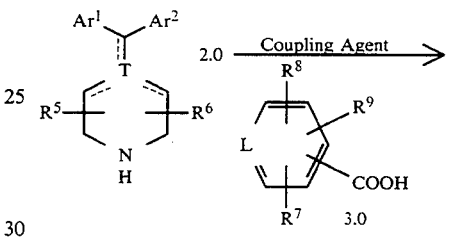

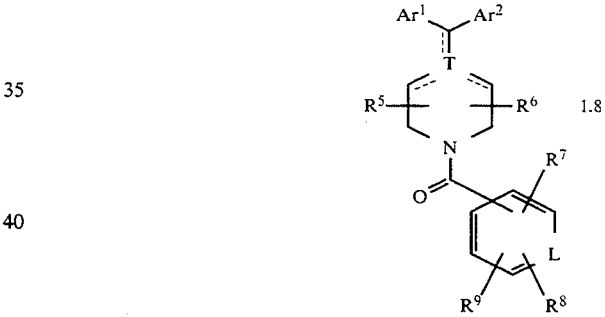

The reaction is usually conducted in an inert solvent such as tetrahydrofuran (THF) or methylene chloride at a temperature between 0° C. and reflux, preferably at about room temperature. When the coupling agent is DCC or DEC, the reaction may be run in the presence of 1-hydroxybenzotriazole (HOBT).

B. A compound of formula 2.0 may also be reacted with a compound of formula 4.0 in the presence of base to produce compounds 1.0 of structural formula 1.8:

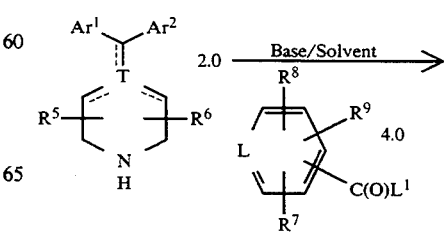

-continued

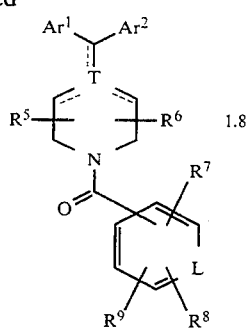

Representative examples of appropriate bases am pyridine and triethylamine. $L^1$ designates a suitable leaving group. For example, a compound of compound 4.0 may be an acyl halide (e.g., $L^1$ represents halo) or an acyl anhydride, (e.g., $L^1$ is —O—C(O)—R' where R' is alkyl or aryl). Compounds of the formula 4.0 are produced by standard methods known in the art from compounds of formula 3.0. For example, treatment of compound 3.0 with oxalyl chloride in an inert solvent would provide compound 4.0 where $L^1$=Cl.

C. Compounds 1.0 of the formula 1.9 may be prepared directly by reacting the N-alkyl (preferably N-methyl) derivative 5.0 with a compound of formula 4.1:

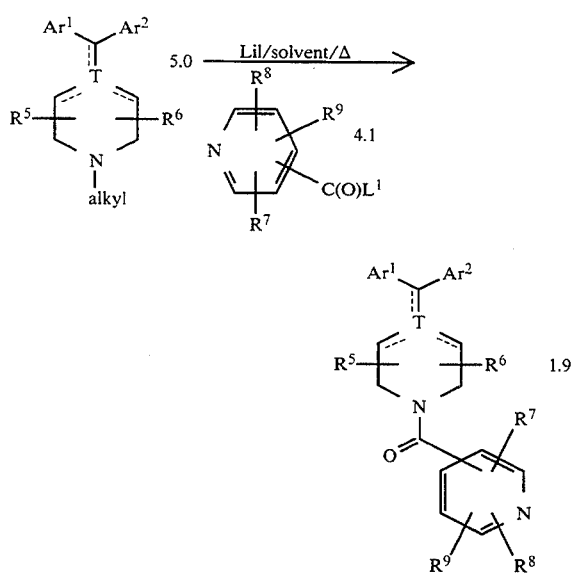

Preferably, the reaction is run in the presence of an appropriate nucleophile (e.g. LiI, etc.) in an inert solvent (e.g., toluene, dioxane or xylenes). $L^1$ is a suitable leaving group such as halo or OC(O)R' where R' is as defined above. An appropriate base, may be added, and heating is usually required. Typically, a temperature ranging from 50°–300° C. (preferably 100°–175° C.) is utilized depending on the boiling point of the solvent.

D. A compound 1.0 of the formula 1.10 can be prepared from a compound of the formula 1.9. This is accomplished with an appropriate oxidizing agent in an inert solvent such as meta-chloroperbenzoic acid (MCPBA) in methylene chloride or hydrogen peroxide in acetic acid. The reaction is usually conducted anywhere from −15° C. to reflux. This method is limited to certain cases since oxidation of other basic amino groups that may be present in the molecule may also occur. Compounds of the formula 1.9 where L is nitrogen (L=N) are prepared as described in methods A to C above.

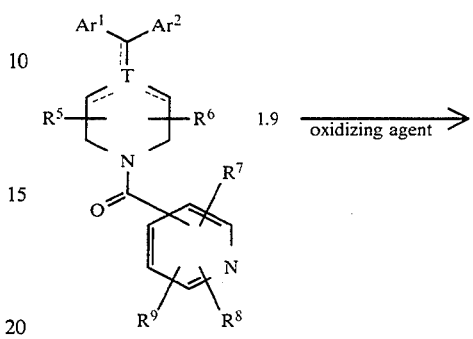

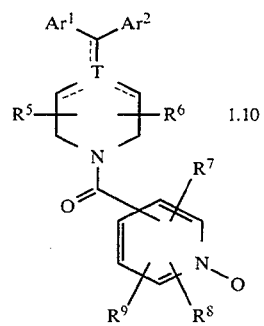

E. Compounds 1.0 of the structural formula 1.11 are best prepared via alkylation of the N-H piperidines 2.0 as illustrated below. Treatment of 2.0 with the appropriately substituted reagent 6.0, wherein J is a leaving group such as halo, mesyl or tosyl, provides the product 1.11. The reaction is usually conducted in an inert solvent such as tetrahydrofuran or methylene chloride at a suitable temperature, usually at reflux, although lower temperatures can sometimes be employed. An appropriate base is usually present such as triethylamine or pyridine although in some cases it is not necessary. The appropriately substituted pyridyl reagent of formula 6.0 can be prepared from the corresponding alcohol using well known procedures (e.g., methanesulfonyl chloride in triethylamine for $J=OSO_2CH_3$ and triphenylphosphine/carbon tetrabromide for J=Br).

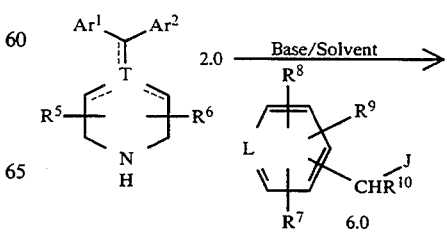

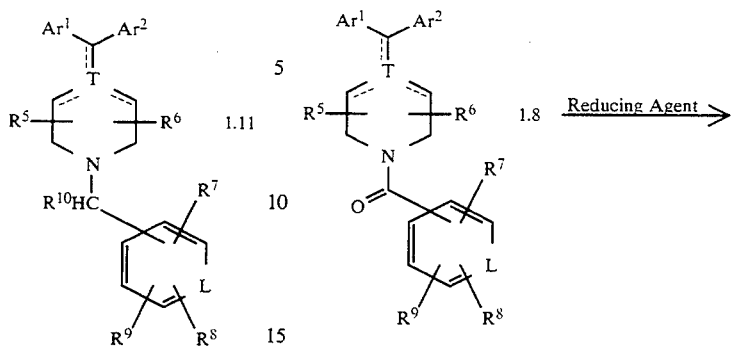

F. Alternatively, many of the compounds 1.0 of structural formula 1.11 can be prepared via reductive amination of the unsubstituted piperidine 2.0 with the appropriately substituted pyridine carboxaldehyde or ketone of the formula 7.0 as illustrated below.

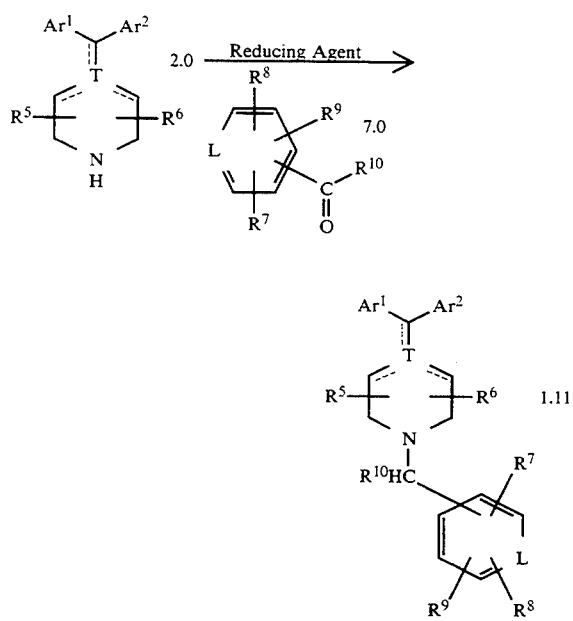

The reaction is typically carded out in a polar solvent such as R'OH, e.g., methanol or ethanol, optionally in the presence of a water scavenger such as 3 Å molecular sieves. The presence of a reducing agent such as $NaCNBH_3$ or $H_2/Pd-C$ is necessary for reduction of the intermediate Schiff base. Temperatures for the reaction are typically held between 0°–100° C. depending on the solvent employed and nature of 7.0.

G. Some of the compounds 1.0 of the formula 1.12 can be prepared via reduction of the corresponding amides 1.8 where Z is oxygen as illustrated below:

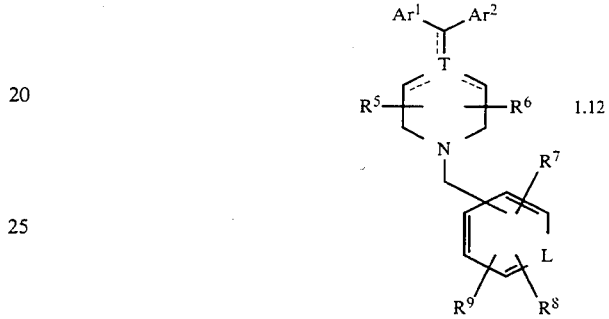

Treatment of the amide 1.8 with a reducing agent such as lithium aluminum hydride or similar reducing agent reduces the carbonyl to provide the compound of formula 1.12. The reaction is typically carded out in an inert solvent like tetrahydrofuran or diethyl ether at a temperature range of 0° C. to reflux. This method is limited to cases where the reducing agent will not reduce other functional groups that may be present in the molecule such as esters and ketones. The appropriately substituted amide 1.8 is obtained as discussed above.

H. Compounds 1.0 of the structural formula 1.13 are best prepared from the corresponding compounds of the invention 1.8 where Z is oxygen (Z=O) using a sulfurating agent such as $P_2S_5$ or Lawesson's reagent. The reaction may take place at elevated temperature in pyridine, toluene or other suitable solvents although lower temperatures can sometimes be employed.

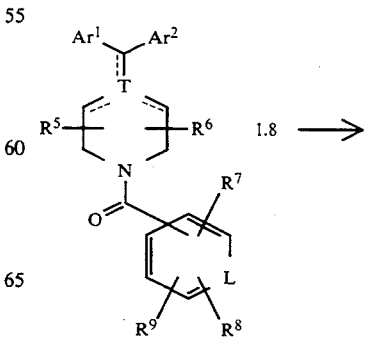

-continued

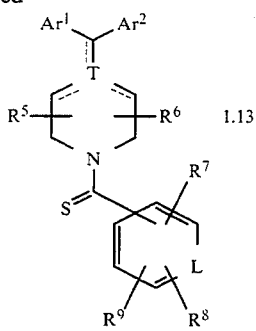
1.13

Compounds of the general formula 2.0 are prepared by removal of the carbamoyl moiety (i.e., $CO_2R''$ where $R''$ is alkyl, substituted alkyl (such as $CHClCH_3$ or $CH_2CCl_3$) or aryl) from the corresponding carbamate 8.0 via either acid (e.g., $HCl/H_2O$/reflux) or base (e.g., $KOH/H_2O$/reflux or alkaline metal carbonates) hydrolysis as illustrated below:

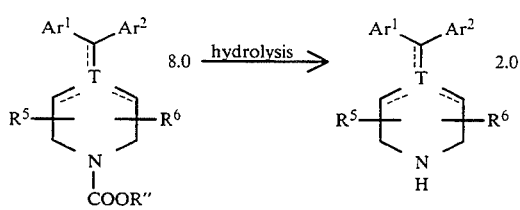

Alternatively, depending upon the nature of $R''$, as determined by one skilled in the art, compound 8.0 may be treated with an organometallic reagent (e.g., $CH_3Li$ for $R''=CH_3$), with a reductive reagent (e.g., Zn in acid for $R''=CH_2CCl_3$), with an alcohol or water (e.g., for $R''=CHClCH_3$), or with hydrogen and a noble metal catalyst such as palladium on carbon (e.g., Pd/C and $H_2$ for $R''$=aralkyl such as benzyl, etc.) to form compounds of formula 2.0.

Compound 8.0 may be prepared from the N-alkyl (preferably N-methyl) compound shown as formula 5.0 below, in the manner disclosed in U.S. Pat. Nos. 4,282,233 and 4,335,036 and in WO 88/03138 for similar compounds:

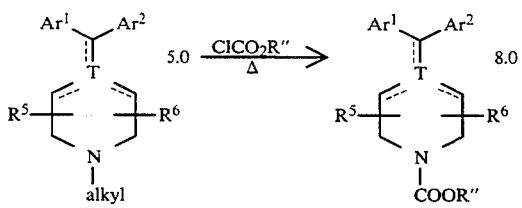

where $R''$ is as defined above. For example, the compound of formula 5.0 can be reacted with the corresponding alkyl chloroformate in an inert solvent such as toluene at a suitable temperature, e.g., 50° to 100° C. to form a compound of formula 8.0.

It also will be apparent to one skilled in the art that there are other methods for converting a compound of formula 5.0 to compound 2.0. For example, treatment of compound 5.0 with phosgene followed by aqueous acid produces the unsubstituted piperidine 2.0. Alternatively, treatment of a compound of formula 5.1 below with BrCN via von Braun reaction conditions would provide nitrile 9.0 as illustrated below. Subsequent hydrolysis of the nitrile 9.0 under either aqueous basic or acidic conditions will produce a compound of formula 2.0. This method is preferable when there is substitution on the piperidine or piperazine ring.

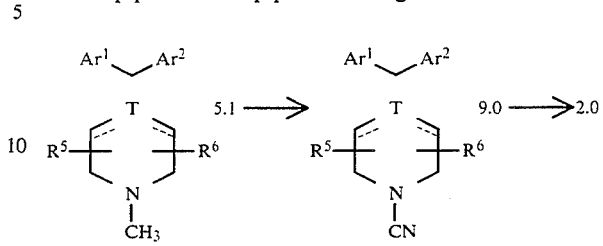

There are many known methods which can be used to prepare compounds of the type 5.0 which are reported in the literature [See for example, U.S. Pat. No. 2,739,968; U.S. Pat. No. 3,956,296; U.S. Pat. No. 4,032,642; U.S. Pat. No. 3,922,276; U.S. Pat. No. 3,956,296; E.P. Patent No. 113,226; and Tetrahedron, 44, 6197 (1988)]. Below we briefly describe a few methods which were used to prepare compounds of the type 5.0.

PREPARATION OF DOUBLE BOND COMPOUNDS

Compounds of the type 5.2 (where T equals carbon having a double bond attached thereto) can be prepared by several methods.

Compounds of the type 5.2 can be prepared from the corresponding alcohol 10.0 by a variety of either acidic or basic conditions. For example, treatment of compound 10.0 with polyphosphoric acid at elevated temperature (T=150°-200° C.) can dehydrate the alcohol to produce the olefin 5.2. Other acids such as trifluoromethanesulfonic acid or sulfuric acid may also be used at a variety of temperatures depending on the nature of compound 10.0 and the acid employed.

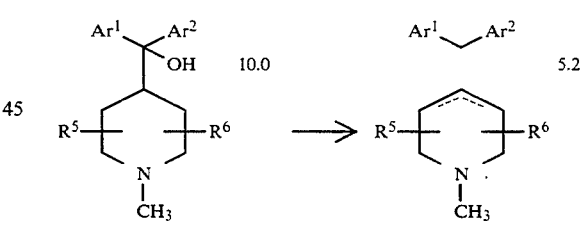

The alcohol 10.0 can be prepared via the treatment of ketone 11.0 with the appropriate metalated reagent 12.0 (such as a Grignard reagent where M=MgX and X is halo) in an inert solvent such as ether or tetrahydrofuran. The reaction may be refluxed if necessary after which it is quenched to produce the alcohol 10.0. The metalated reagent 12.0 can be prepared via usual methods from the corresponding halo derivative.

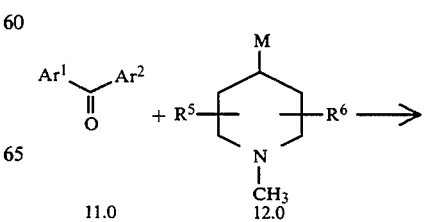

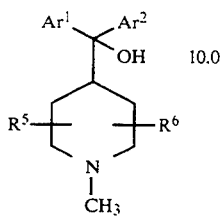

Another method for the preparation of compounds of type 5.2 involves treatment of the appropriately substituted aryl piperidyl ketone 18.0 or 18.1 with the appropriately substituted metalated aryl derivative 16.0 or 16.1 to produce the alcohol 10.0, which in turn can be converted to 5.2 as discussed above. The reaction is usually conducted in an inert solvent such as tetrahydrofuran or diethyl ether at temperatures ranging from −78° C. to reflux, but typically at 0° C. A variety of metalated reagents can be used in this process, for example, a Grignard reagent where M is as defined above.

substituted acid chloride 13.0 and 13.1 and the appropriately substituted aryl compound 14.0 or 14.1. The reaction is carried out under usual Friedel—Crafts conditions in an inert solvent and in the presence of a Lewis acid such as aluminum chloride. Alternatively, the reaction can be done under basic conditions wherein the appropriately substituted metalated aryl ring compound 16.0 or 16.1 (such as a Grignard reagent where M is as defined above) is treated with the appropriately substituted nitrile 15.0 or 15.1. The reaction is usually conducted in an dry aprotic solvent such as tetrahydrofuran or diethylether at a variety of temperatures typically ranging from 0° C. to reflux depending on the solvent of choice. The resultant imine which is produced from this reaction is simply hydrolyzed in aqueous acid to produce the desired diaryl ketone 11.0.

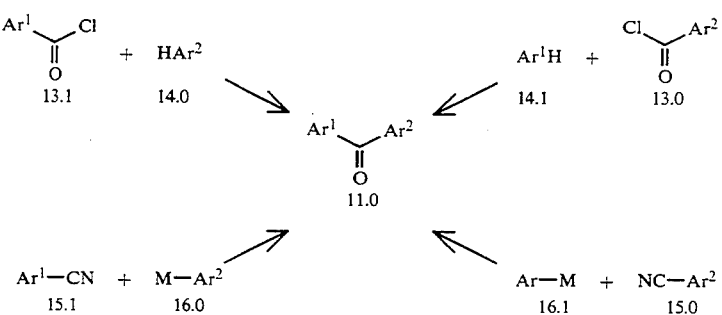

In addition, compounds of formula 11.0 where Ar² is

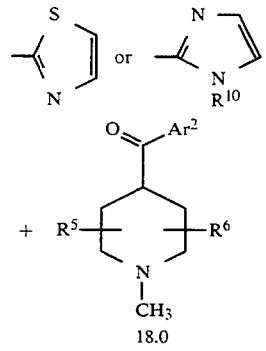

(i.e., compounds 11.1 and 11.2) can be prepared by the methods illustrated below:

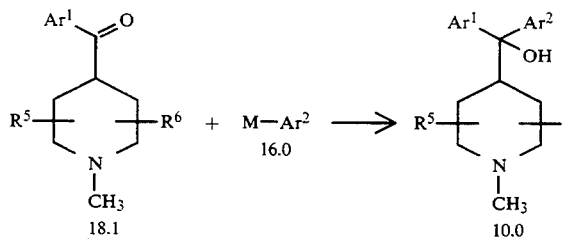

There are many methods known for the preparation of the various substituted diaryl ketones 11.0. The choice of which method to use depends largely on the nature of Ar¹ and Ar² and on the substitution in the aryl rings. For example, they can be prepared via a Friedel—Crafts acylation between the appropriately

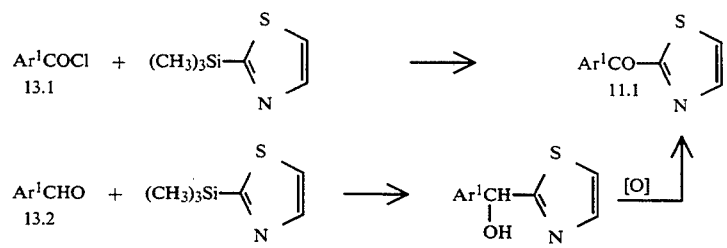

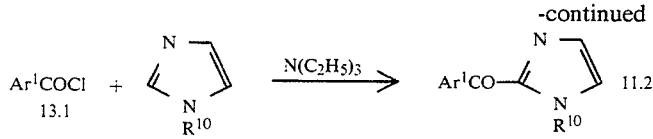

The preparations of compounds 11.1 and 11.2 respectively appear in *J. Org. Chem.* 53, 1748–1761 (1988) and *Ann. Chem.* 145–158 (1988).

A number of compounds of the type 5.2 may be prepared via low valent titanium mediated coupling of the two appropriately substituted ketones 11.0 and 17.0 as reported in Tetrahedron, 44, 6197 (1988). The two ketones are treated with a mixture of titanium trichloride and lithium in a polar solvent such as dimethoxyethane at room temperature to produce the corresponding olefin 5.2.

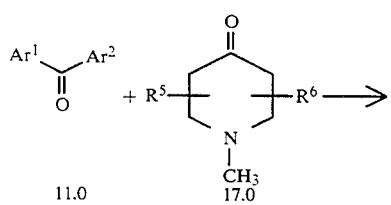

largely on the nature of $Ar^1$ and $Ar^2$ and on the substitution present in the aryl rings. For example, they can be prepared via a Friedel-Crafts acylation between the appropriately substituted acid chloride 19.0 with the appropriately substituted aryl compound 14.0 or 14.1. The reaction is done under usual Friedel-Crafts conditions in an inert solvent and in the presence of a Lewis acid such as aluminum chloride. Alternatively, the reaction can be done under basic conditions wherein the appropriately substituted metalated aryl compound 16.0 or 16.1 (such as a Grignard reagent where M is as defined above) is treated with the appropriately substituted nitrile 20.0. The reaction is usually conducted in an dry aprotic solvent such as tetrahydrofuran or diethyl ether at a variety of temperatures typically ranging from 0° C. to reflux depending on the solvent of choice. The resultant imine which is produced from this reaction is simply hydrolyzed in aqueous acid to produce the desired aryl piperidyl ketone 18.0 or 18.1. Conversely, the metalated species and nitrile can be interchanged so that the piperidine is metalated (formula 12.0) and the aryl compound is substituted with the nitrile (formula 15.0 or 15.1). This reaction is conducted under the same conditions as described above to produce the imine which is hydrolyzed to produce the aryl piperidyl ketone 18.0 or 18.1.

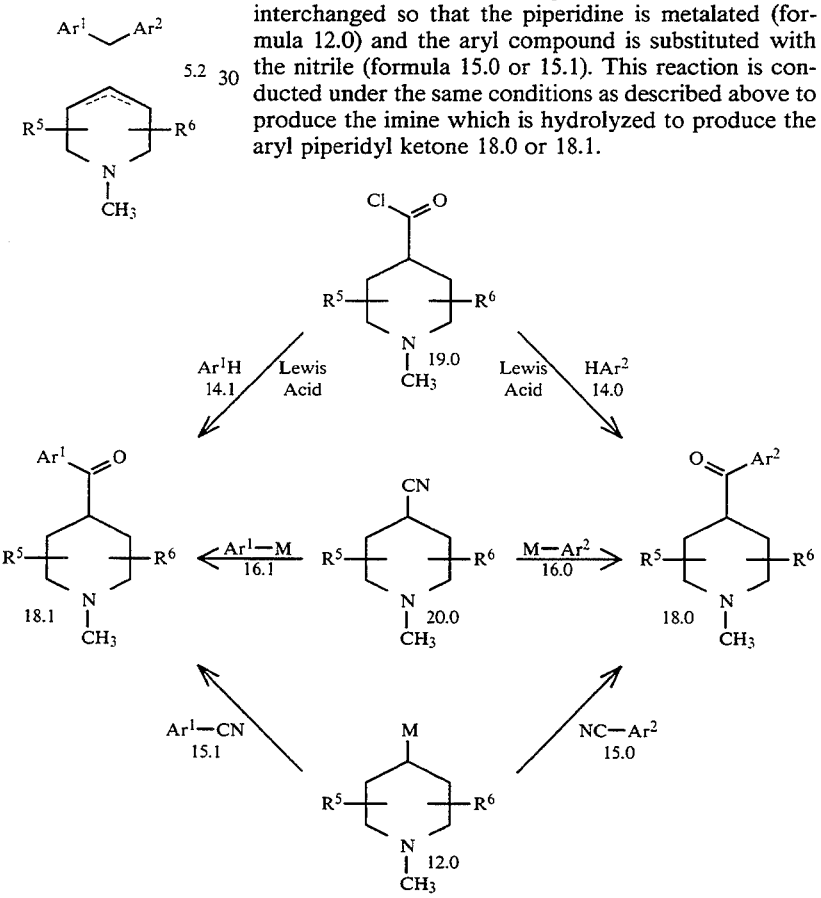

There are many methods known for the preparation of the various substituted aryl piperidyl ketones 18.0 or 18.1. The choice of which method to use depends

PREPARATION OF SINGLE BOND COMPOUNDS

To prepare intermediate compounds of the type where T equals CH and a single bond exists between T and the carbon atom bridging the two aryl groups Ar¹ and Ar², a variety of methods are disclosed in the literature. A few of the preferred methods are as follows.

Compounds of the type 22.0 where R''' represents CH₃ may be prepared from the olefin derivatives of the type 21,0 (i.e., of formula 5.2) via catalytic hydrogenation using a variety of catalysts such as Pt, Rh, Ru, or Pd on various supports, For example, treatment of compound 21.0 where R''' is CH₃ with hydrogen in the presence of 5% Pd on carbon in an inert solvent such as methanol or ethanol results in reduction of the double bond to produce compound 22.0 (R'''=CH₃, i.e., a compound of formula 5.3 below).

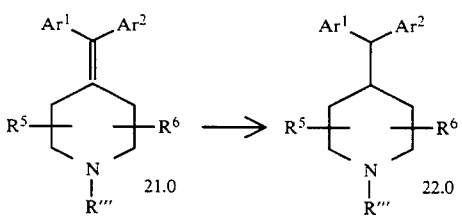

Alternatively, in certain cases, depending on the nature of the substituents, one can hydrogenate a compound of the formula 21.0 above where R''' represents

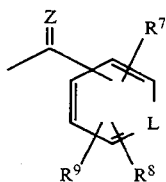

(i.e., a compound of formula 1.0) or where R''' represents H (i.e., a compound of formula 2.0) to produce the corresponding single bond compound of the formula 22.0. The conditions for this conversion would be the same as discussed above.

Compounds of the type 5.3 can be prepared from the corresponding alcohol derivatives 10.0 via reductive removal of the hydroxy group under a variety of conditions. For example, treatment of compound 10.0 with triethylsilane as described by Kishi [J. Am. Chem. Soc., 104, 4976 (1982)]can produce the corresponding compound 5.3.

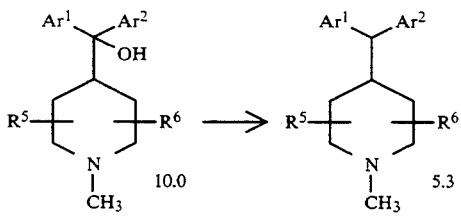

A third method for the preparation of compound 5.3 is by the treatment of the appropriately substituted Grignard reagent or other similar metalated reagent 12.0 with the appropriately substituted derivative 23.0 (L²=halo or other suitable leaving group). These reactions generally are conducted in an inert solvent such as ether, toluene, or THF at a temperature range of about −78 to about 50° C. to produce the compound 5.3. Alternatively, the metalating substituent and the leaving substituent L² as defined above could be interchanged as in Compounds 24.0 and 25.0 below and reacted under the same conditions to produce the same compound 5.3.

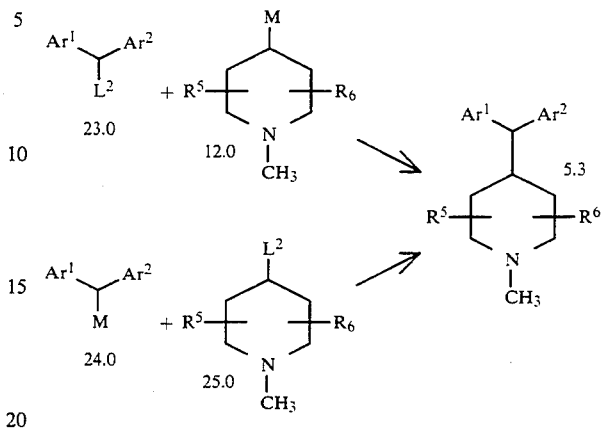

The appropriately substituted derivative 23.0 is simply prepared from the corresponding alcohol 26.0 by reaction with a halogenating agent or activating agent. A variety of methods may be used to convert an alcohol to the corresponding halide depending on the L² group desired and the nature of the alcohol. For example, if the chloro derivative (L²=Cl) is desired, one may simply treat the alcohol 26.0 with a chlorinating agent such as thionyl chloride, phosphorous pentachloride, phosphorous trichloride or phosphorous oxychloride, in an inert solvent such as toluene to produce the corresponding chloro derivative 23.0. An activating agent such as methanesulfonyl chloride, benzene or toluene sulfonyl chloride or trifluoromethanesulfonyl chloride may also be employed to produce other suitable leaving groups L² in compound 23.0.

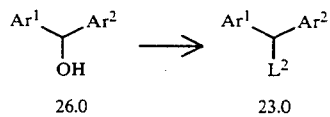

The alcohol 26.0 in turn is obtained from the corresponding diaryl ketone 11.0 via a variety of reductive methods. Various reducing agents such as lithium aluminum hydride, sodium or potassium borohydride, lithium, etc., can be used and their choice largely depends on the substituents present on the diaryl ketone. The choice of solvent usually depends on the reducing agent employed.

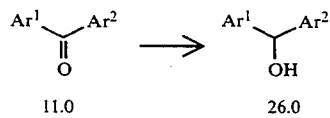

A compound of the formula 26.0 can be prepared by reacting a compound of the formula 28.0 or 28.1 with an aldehyde of the formula 27.0 or 27.1 as set out below, wherein M¹ is MgX₂ and X is halo or where M¹ is Li, trialkylsilyl, etc.

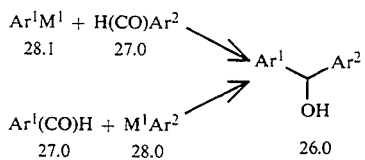

PREPARATION OF PIPERAZINE COMPOUNDS

To prepare intermediate compounds where T equals nitrogen and a single bond exists between T and the carbon atom bridging the two aryl groups, a variety of methods are again disclosed in the literature. A few of the preferred methods are as follows.

Compounds of the formula 29.0 below are best prepared via alkylation of the appropriately substituted piperazine compound 30.0 with compound 23.1 containing the appropriately substituted halide or other similar leaving group $L^1$ as defined above (e.g., halo, tosyloxy or mesyloxy) and where $R'''$ is as defined above. The reaction usually is conducted in an inert solvent such as tetrahydrofuran or toluene, typically at a temperature range of ambient to reflux to produce the alkylated piperazine. The reaction can be conducted in the presence of a base such as triethylamine or potassium carbonate, although in certain cases it can be omitted. If $R'''$ is the appropriately substituted nicotinamide or pyridylmethyl moiety, then the resultant alkylated piperazine of formula 29.0 is a compound of the invention 1.0. If however, $R'''$ is either hydrogen or methyl then the resultant hydrogenated or alkylated piperazine 29.0 must be convened to the compounds of the invention of formula 1.0 as disclosed above.

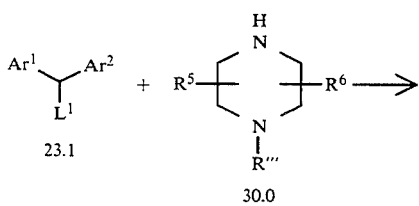

An alternative route for generating the hydrogenated or alkylated piperazines of formula 29.0 is by reductive amination of the diaryl ketone 11.0 with the appropriately substituted piperazine 30.0. The reaction typically is carried out in a polar solvent, such as methanol or ethanol optionally in the presence of a water scavenger such as 3 Å molecular sieves. The intermediate iminium salt is reduced to the hydrogenated or alkylated piperazines of formula 29.0 by employing a variety of reducing agents such as $NaCNBH_3$ or catalytic hydrogenation, for example, hydrogen over Pd/C.

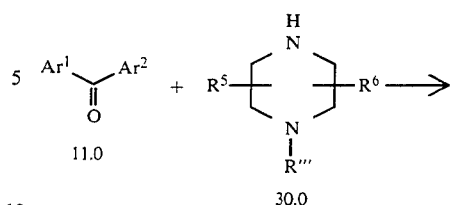

In the above processes, it is sometimes desirable and/or necessary to protect certain $R^1$, $R^2$, $R^{3'}$ $R^4$, $R^5$, $R^6$, etc., groups during the reactions. Certain protecting groups are employed in the above processes but, as those skilled in the art will recognize, other protecting groups may be used in their place. Conventional protecting groups are operable as described in Greene, T. W., "Protective Groups In Organic Synthesis," John Wiley & Sons, New York, 1981. For example, the groups listed in column 1 of Table 1 below may be protected as indicated in column 2 of the table:

TABLE 1

PROTECTED GROUPS

| 1. GROUP TO BE PROTECTED | 2. PROTECTED GROUP |
|---|---|
| —COOH | —COOalkyl, —COObenzyl, —COOphenyl, 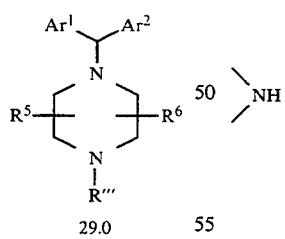 |
| $\diagdown$NH$\diagup$ | $\diagdown$NCOalkyl, $\diagdown$NCObenzyl, $\diagdown$NCOphenyl |
| $\diagdown$CO$\diagup$ | 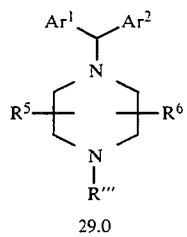 |
| —OH | —O-(THP), —OCH$_2$phenyl, —OCH$_3$, OSi(CH$_3$)$_2$(t-Bu). |

TABLE 1-continued

PROTECTED GROUPS

| 1. GROUP TO BE PROTECTED | 2. PROTECTED GROUP |
|---|---|
| —NHR, wherein R is any substituent on an amino group within the scope of the claims | 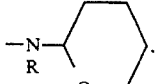  —NR—CO—CF$_3$, —NRCOCH$_3$, —NRCH$_2$-C$_6$H$_5$ |
| —NH$_2$ | 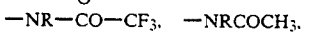  —NH—C(O)—O(t-Bu) |

Other protecting groups well known in the art also may be used. After the reaction or reactions, the protecting groups may be removed by standard procedures.

The compounds of the invention possess platelet-activating factor ("PAF") and histamine antagonistic properties. They are, therefore, useful when PAF and/or histamine are factors in the disease or disorder. This includes allergic diseases such as asthma, allergic rhinitis, adult respiratory distress syndrome, urticaria and inflammatory diseases such as rheumatoid arthritis and osteo-arthritis. For example, PAF is an important mediator of such processes as platelet aggregation, smooth muscle contraction (especially in lung tissue), eosinophil chemotaxis, vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. In Vitro Studies
Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 ml) was collected from healthy male donors in an anticoagulant solution (5 ml) containing sodium citrate (3.8%) and dextrose (2%). Blood was centrifuged at 110×g for 15 min. and the supernatant platelet-rich plasma (PRP) carefully transferred into a polypropylene tube. Platelet-poor-plasma (PPP) was prepared by centrifuging PRP at 12,000×g for 2 min. PRP was used within 3 hr. of drawing the blood.

PAF was dissolved in chloroform:methanol (1:1, v/v) at a concentration of 2 mg/ml and stored at −70° C. An aliquot of this solution was transferred to a polypropylene tube and dried under a flow of nitrogen gas. To the dried sample was added Hepes-saline-BSA (BSA=bovine serum albumen) buffer (25 mM Hepes, pH 7.4, 1254 mM NaCl, 0.7 mM MgCl2 and 0.1% BSA) to obtain a 1 mM solution. The solution was sonicated for 5 min. This stock solution was further diluted to appropriate concentrations in Hepes-saline-BSA buffer. Collagen and adenosine diphosphate (ADP) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer. PRP (0.45 ml) in aggregometer cuvettes was continually stirred (37° C.). Solutions (50 μL) of test compounds or vehicle were added to the PRP and, after incubation for 2 min., 10–15 μl aliquots of PAF solution were added to achieve a final concentration of $1-5 \times 10^{-8}$M. In different experiments the aggregatory response was kept within a set limit by varying the concentration of PAF. Incubations were continued until the increase in light transmission reached a maximum (usually 2 min.). This increase in light transmission reflecting platelet aggregation is transmitted to a computer. The computer calculates the slope of transmission change, thus providing the rate of aggregation. Values for inhibition were calculated by comparing rates of aggregation obtained in the absence and the presence of the compound. For each experiment, a standard PAF antagonist such as 8-chloro-6,11-dihydro-11-(1-acetyl-4-piperidylidene)-5H-benzo[5,6]cyclohepta[1,2-b]pyridine was used as a positive control.

Compounds that inhibit PAF-induced aggregation were tested against several other aggregating agents including collagen (0.2 mg/ml) and ADP (2 μM). Compounds showing no activity against these latter agents were considered to be specific PAF antagonists. Results are shown in TABLE II below.

B. In Vivo Studies: Agonist-Induced Responses
Spasmogen-Induced Bronchospasm in Guinea Pigs Male Hartley guinea pigs (450–550 g) were obtained from Charles River Breeding Laboratories. The animals were fasted overnight and the following day were anesthetized with 0.9 ml/kg i.p. of dilaurethane (containing 0.1 g/ml diallylbarbituric acid, 0.4 g/ml ethylurea and 0.4 g/ml urethane). The left jugular vein was cannulated for the administration of compounds. The trachea was cannulated and the animals were ventilated by a rodent respirator at 55 strokes/min. with a stroke volume of 4 ml. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg) or PAF (0.4 μg/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in TABLE II below for representative examples of compounds of the present invention. The first two compounds in TABLE II are known compounds and are included for comparison purposes.

TABLE II

| | PAF Antagonism (in vitro) IC$_{50}$(μM) | Agonist Bronchospasm (in vivo) - oral | | | |
|---|---|---|---|---|---|
| | | PAF | | Histamine | |
| | | Dose | % Inhibition | Dose | % Inhibition |
| 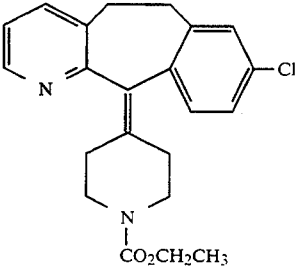 | 175 | 10 mg/kg | <50 | 1 mg/kg | >50 |
| 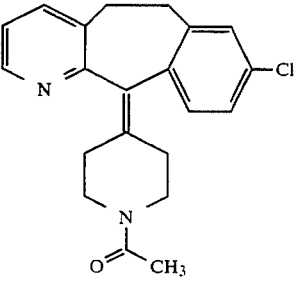 | 0.61 | 3 mg/kg | 4 | 3 mg/kg | 48 |

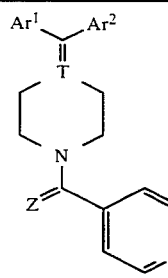

| Ar$^1$ | Ar$^2$ | T | Z | PAF Antagonism (in vitro) IC$_{50}$(μM) | Agonist Bronchospasm (in vivo) - oral | | | |
|---|---|---|---|---|---|---|---|---|
| | | | | | PAF | | Histamine | |
| | | | | | Dose | % Inhibition | Dose | % Inhibition |
| 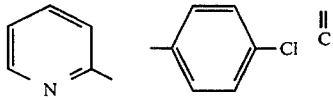 | 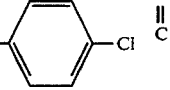 | | O∥C | 0.5 | 3 mg/kg | 100 | 3 mg/kg | 0 |
|  | 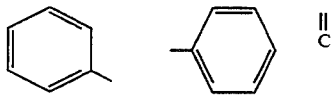 | | O∥C | 3 | 3 mg/kg | 44 | 3 mg/kg | 0 |
|  |  | | O↓N | 1 | 3 mg/kg | 99 | 3 mg/kg | 30 |
| 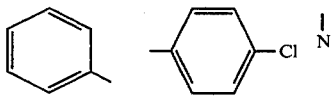 | 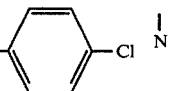 | H$_2$ | ∥C | 12 | 3 mg/kg | 18 | 3 mg/kg | 95 |
|  | 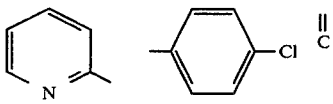 | | O↓N | 0.2 | 3 mg/kg | 22 | N.T. | |

TABLE II-continued

| | | | | | | |
|---|---|---|---|---|---|---|
| 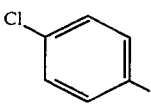 |  | O | 1 | 3 mg/kg | 73 | 10 Mg/kg | 25 |
|  | 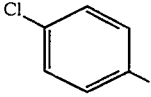 | ‖C | 2 | N.T | | N.T. | |
|  |  | H₂ ‖C | 20 | N.T | | N.T. | |
| 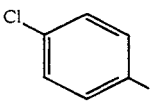 |  | H₂ | 15 | N.T | | N.T. | |
|  | 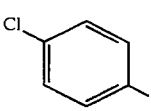 | H₂ | 12 | N.T | | N.T. | |
|  |  | O ‖C | 0.5 | N.T | | N.T. | |
| 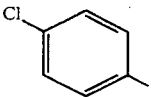 |  | H₂ ‖C | 35 | N.T | | N.T. | |
|  | 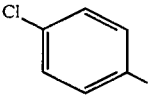 | O ‖C | 1 | N.T | | N.T. | |

The compounds of structural formula 1.0 exhibit PAF antagonist and antihistaminic properties to varying degrees, i.e., certain compounds have strong PAF antagonistic activity, but have weaker antihistaminic activity. Other compounds are strong antihistamines but weaker PAF antagonists. Several of the compounds are both strong PAF antagonists and potent antihistamines. Consequently, it is within the scope of this invention to use each of these compounds when clinically appropriate. For example, if a strong PAF antagonist is required, but weaker antihistaminic activity is necessary, such a compound could be chosen by the clinician. Alternatively, if both potent PAF antagonism and antihistaminic activity are required, a different compound of the invention would be utilized by the clinician.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and Solids in powder form, which may be in combination with a pharmaceutically acceptable carrier, such as an inert compressed gas.

Also included are solid form preparations which are intended to be convened, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 rag, more preferably from about 1 mg. to 300 rag, according to the particular application. The appropriate dosage can be determined by comparing the activity of the compound with the activity of a known antihistaminic compound such as 8-chloro-6,11-dihydro-11-(1-ethoxycarbonyl-4-piperidylidene)-5H-benzo[5,6]cyclohepta[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 1500 mg/day preferably 10 to 750 mg/day, in two to four divided doses to achieve relief of the symptoms. The compounds are non-toxic when administered within this dosage range.

The invention disclosed herein is exemplified by the following preparative examples, which should not be construed to limit the scope of the disclosure. Alternative pathways and analogous structures within the scope of the invention may be apparent to those skilled in the art.

PREPARATIVE EXAMPLE 1A

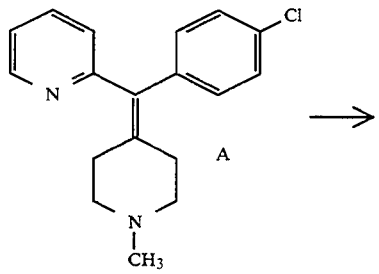

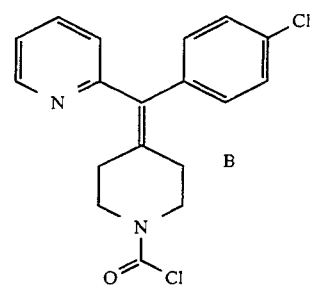

Phosgene was bubbled through a mixture of 9.3 g (31.1 mmol) of Compound A above (U.S. Pat. No. 2,739,968) in 100 ml of carbon tetrachloride at room temperature for a period of 25 minutes. The mixture was then refluxed for 2 hours, after which it was diluted with ether and the resultant solid filtered off. The filtrate was concentrated in vacuo to yield 8.4 g (78%) of Compound of formula B above as a red brown oil.

PREPARATIVE EXAMPLE 1B

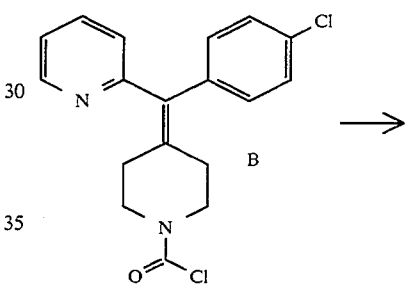

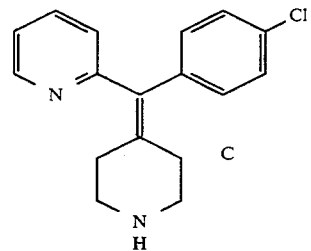

A mixture of 7.3 g (21.0 mmol) of Compound B above in 100 ml of 10% aqueous hydrochloric acid was heated at 100° C. for 30 minutes. The solution was cooled to room temperature, basified, and extracted with ether. The organic portion was dried, filtered, and concentrated in vacuo to yield Compound C above as a brown oil.

PREPARATIVE EXAMPLE 2A

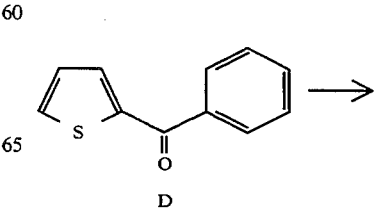

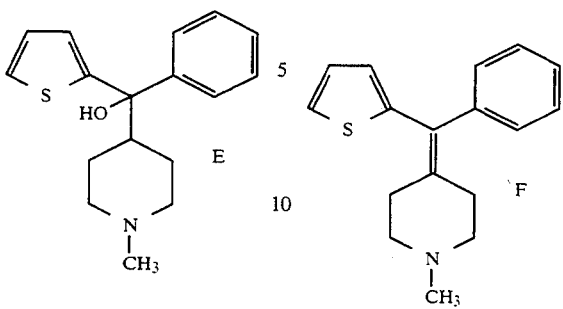

To a mixture of the Grignard reagent prepared from 490 g of 1-methyl-4-chloropiperidine in 7000 mL of THF at 0° C. was slowly added a solution of 376 g of 2-benzoylthiophene (i.e., compound D) in 1200 mL of dry tetrahydrofuran. The mixture was then refluxed overnight. The mixture was partially concentrated and the residue cooled to 0° C., slowly quenched with 2000 mL of saturated aqueous ammonium chloride, and extracted with chloroform. The organic portion was washed with water, dried over sodium sulfate, filtered, and concentrated in vacuo to yield the crude product. It was then triturated with petroleum ether and the resultant solid recrystallized from acetonitrile to yield 284 g of Compound E above as a tan solid: MP 141°–144° C.

PREPARATIVE EXAMPLE 2B

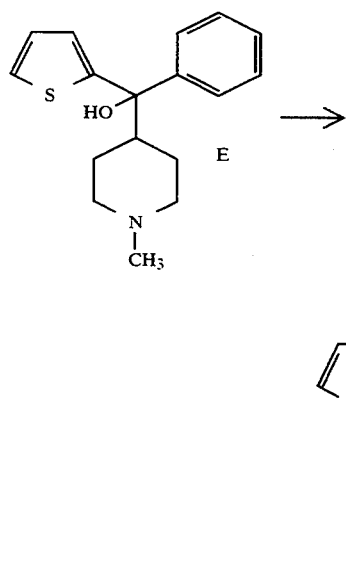

A mixture of 86.1 g (0.3 mole) of Compound E, 860 mL of glacial acetic acid, and 170 mL of concentrated hydrochloric acid was heated on a steam bath for 2 hours. The mixture was concentrated in vacuo and the residue was dissolved in water, basified with 50% aqueous sodium hydroxide, and extracted with ether. The organic portion was washed with water, dried over sodium sulfate, filtered, and concentrated in vacuo to yield 78.0 g of Compound F above as a brown oil.

PREPARATIVE EXAMPLE 2C

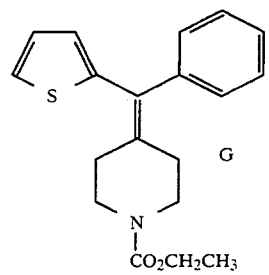

To a mixture of 66.0 g (0.6 mole) of ethyl chloroformate in 700 mL of dry benzene was slowly added a solution of 53.0 g (0.2 mole) of Compound F in 500 mL of dry benzene. The mixture was then refluxed overnight, after which it was cooled and poured into water. The organic portion was isolated, washed with water, dried over sodium sulfate, filtered, and concentrated in vacuo to yield a light brown oil. The crude product was triturated with petroleum ether to provide a solid which was recrystallized from hexane to yield 58.0 g of Compound G above as a solid: MP 79°–83° C.

PREPARATIVE EXAMPLE 2D

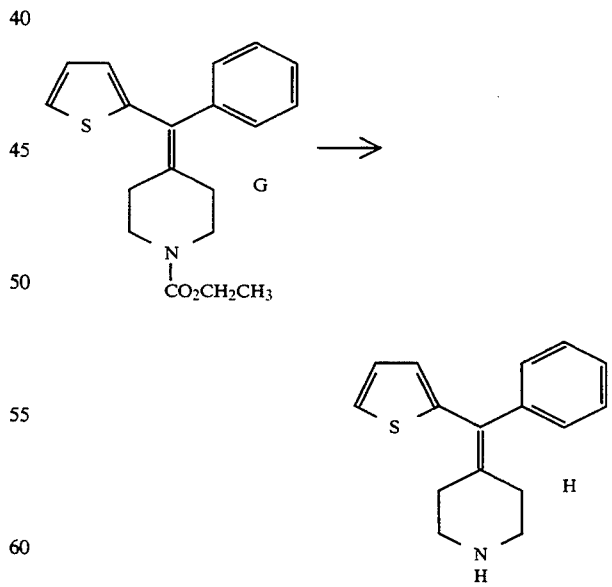

A mixture of 77.0 g (0.234 mole) of Compound G and 77.0 g (1.37 mole) of potassium hydroxide in 2000 mL of ethanol was refluxed overnight. The mixture was concentrated in vacuo and the residue was taken up in water and extracted with ether. The organic portion was isolated, washed with water, dried over sodium sulfate, filtered, and concentrated in vacuo to yield a light brown oil which consisted of a mixture of starting material and compound H. Therefore, the crude product and 75.0 g (1.34 mole) of potassium hydroxide in 2000 mL of propanol was again refluxed overnight. The mixture was concentrated in vacuo and the residue was taken up in water and extracted with ether. The organic portion was isolated, washed with water, dried over sodium sulfate, filtered, and concentrated in vacuo to yield a light brown oil. The crude product was triturated and subsequently recrystallized from petroleum ether to provide 49.0 g of Compound H above as a white solid: MP 67°–69° C.

PREPARATIVE EXAMPLE 3A

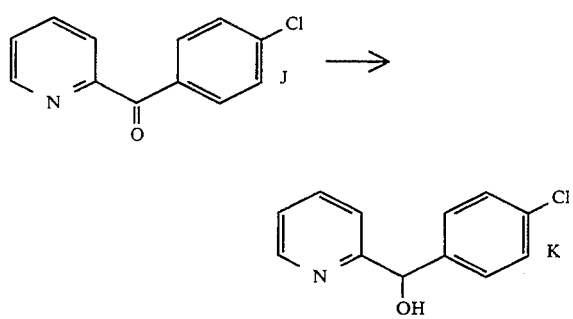

To a mixture of 33.0 g (15.2 mmol) of Compound J above in 1500 ml of methanol at 0° C. was added portionwise 18.0 g (476 mmol) of sodium borohydride. The mixture was then slowly allowed to warm to room temperature and stirred overnight. The reaction mixture was poured into ice-water, saturated with sodium chloride, and extracted with chloroform. The organic portion was washed with water, dried over sodium sulfate, filtered, and concentrated in vacuo to yield a light brown oil which solidified on standing. It was recrystallized from isopropyl ether to afford 32.0 g (97%) of Compound K above as a white solid.

By employing basically the same procedure as outlined above but substituting Compound L (which is available by the method of *J. Org. Chem.* 53, 1748–1761 (1988)) in place of Compound J, Compound M below was prepared.

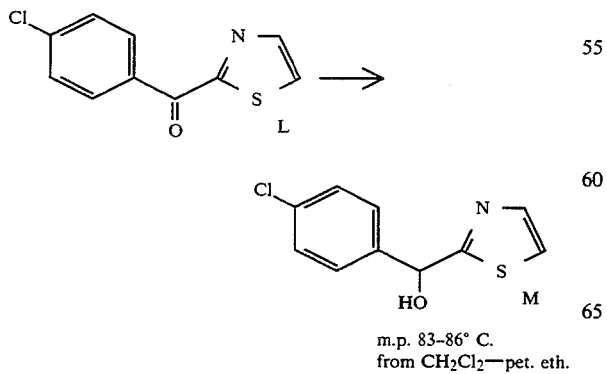

m.p. 83–86° C.
from CH$_2$Cl$_2$—pet. eth.

PREPARATIVE EXAMPLE 3B

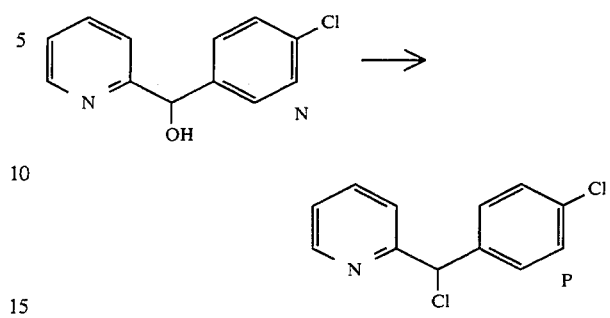

To a mixture of 20.0 g (168 mmol) of thionyl chloride at 10° C. was slowly added a solution of 32.0 g (146 mmol) of Compound N above in 400 ml of dry benzene. The mixture was allowed to warm to room temperature and then stirred for 3 hours, after which 50.0 g (494 mmol) of triethylamine was added with cooling. The reaction mixture was stirred for another 30 minutes and then filtered, and the filtrate was concentrated in vacuo. The residue was distilled (b.p. 134°–136° C./0.5 mm Hg) to afford 18.0 g (52%) of Compound P above as a red oil.

By employing basically the same procedure as outlined above but substituting Compound M in place of Compound N, Compound Q below was prepared.

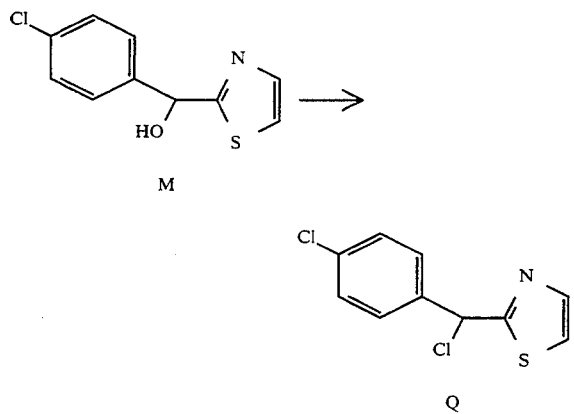

PREPARATIVE EXAMPLE 3C

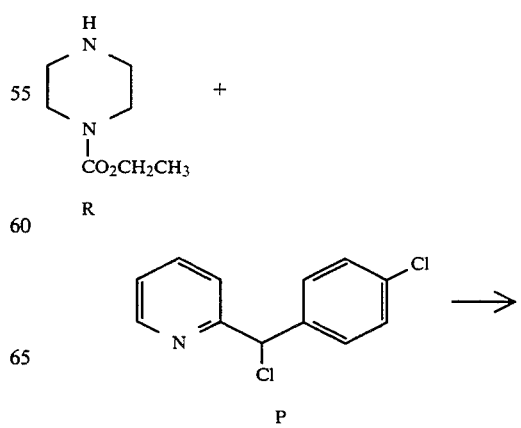

-continued

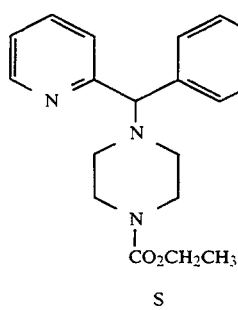

S

To a refluxing mixture of 11.7 g (74.0 mmol) of N-ethoxycarbonylpiperazine (Compound R) and 7.95 g (75.0 mmol) of anhydrous sodium carbonate in 400 ml of dry xylene was slowly added a solution of 18.0 g (75.6 mmol) of Compound P above in 150 ml of dry xylene. The mixture was then refluxed for 40 hours, after which it was cooled to room temperature and extracted with dilute aqueous hydrochloric acid. The aqueous portion was basified with ammonium hydroxide and subsequently extracted with chloroform. The latter organic portion was washed with water, dried over sodium sulfate, filtered, and concentrated in vacuo to yield a brown oil which solidified on standing. The solid was recrystallized from acetonitrile to afford 6.5 g (24%) of Compound S above as a solid.

PREPARATIVE EXAMPLE 3D

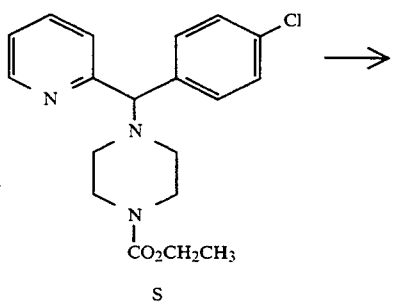

T

A mixture of 2.50 g (6.95 mmol) of Compound S above in 250 ml of 18% aqueous hydrochloric acid was refluxed for 3 days. The mixture was then cooled to room temperature, basified with concentrated aqueous sodium hydroxide, and extracted three times with methylene chloride. The combined organic portions were dried over magnesium sulfate, filtered, and concentrated in vacuo. The residue was purified by flash chromatography [4–5 % methanol saturated with ammonia in methylene chloride] to provide 1.68 g (84%) of Compound T above as an oil.

PREPARATIVE EXAMPLE 4

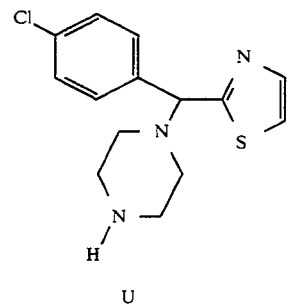

Q

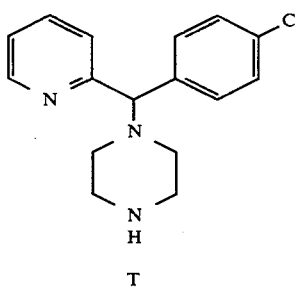

U

A solution of Compound Q above (0.5 g, prepared as described in Preparative Example 3B) in dry tetrahydrofuran (10 ml) was added to a solution of piperazine (2.12 g) in dry tetrahydrofuran (10 ml). The resulting solution was allowed to stir under nitrogen for 18 hrs. at 25° C. The solution was then concentrated, and the residue was basified with concentrated aqueous ammonia, and extracted with dichloromethane and with ethyl acetate. The organic layers were dried (MgSO4), filtered, and concentrated; and the residue was chromatographed over silica gel. Elution of the column with dichloromethane-methanol-aqueous ammonia (98:1.8:0.2, by volume) gave Compound U above.

PREPARATIVE EXAMPLE 5A

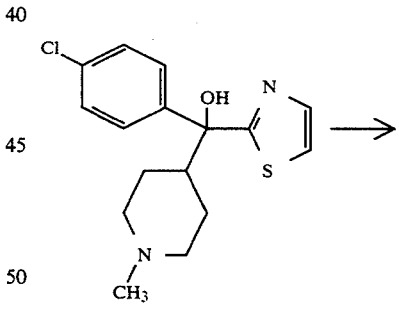

V

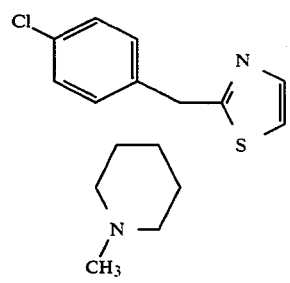

W

Acetyl chloride (2 ml) was added slowly to a hot (ca. 100° C.) solution of Compound V (2.0 g) (which is prepared by basically the same method as described in Preparative Example 2A above) in acetic acid (10 ml) containing acetic anhydride (2 ml). The reaction mixture was then refluxed 2 hrs., cooled, and diluted with water (5 ml). The resulting mixture was concentrated to remove acetic acid, basified with 50% aqueous sodium hydroxide solution, and extracted with dichloromethane. Combined extracts were dried (MgSO₄), filtered through a bed of diatomaceous earth containing activated charcoal, and concentrated. The residue was chromatographed over silica gel, and hexanes-ethyl acetate (20: 80, by volume) eluted Compound W above, m/z 304 (M+).

PREPARATIVE EXAMPLE 5B

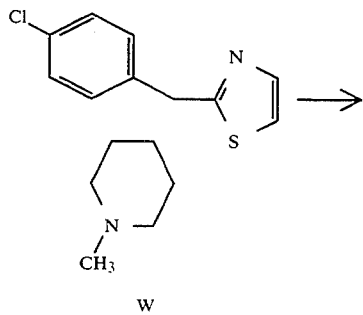

Trichloroethyl chloroformate (3.00 g) was added to a refluxing solution of Compound W above (1.03 g) in dry benzene (40 ml) containing potassium carbonate (0.1 g). The resulting mixture was then refluxed 18 hrs., cooled, and concentrated. A solution of the residue in dichloromethane was washed with water and dilute aqueous sodium bicarbonate solution. The dried (MgSO₄) and filtered organic solution was then evaporated, and the residue was chromatographed over silica gel. Elution of the column with dichloromethane-methanol (9:1, by volume) gave Compound X above, m.p. 141°–145° C. from CH₂Cl2-pet.ether.

PREPARATIVE EXAMPLE 5C

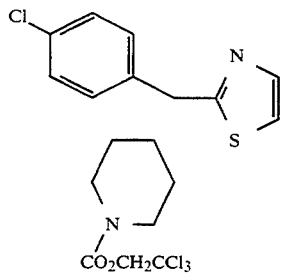

Zinc dust (0.85 g) was added to a solution of Compound X above (1.39 g) in acetic acid (20 ml). The resulting mixture was heated at 80° C. for 2 hours, and was then cooled. The zinc was collected by filtration, washed with acetic acid and with water; and the filtrate and washings were combined. The resulting solution was concentrated, and the residue was basified with 50% sodium hydroxide solution. The basic aqueous solution was then extracted with dichloromethane. Combined organic extracts were dried (MgSO₄), filtered, and concentrated to give an oil. Chromatography of the oil over silica gel and elution with CH₃OH-ethyl acetate (9:1) gave Compound Y above as an oil, m/z 290 (M+).

By employing basically the same procedures as outlined above in Preparative Examples 5A–5C, but substituting Compounds A¹ and B¹ in place of Compound V, Compounds C¹ and D¹, respectively, below were prepared.

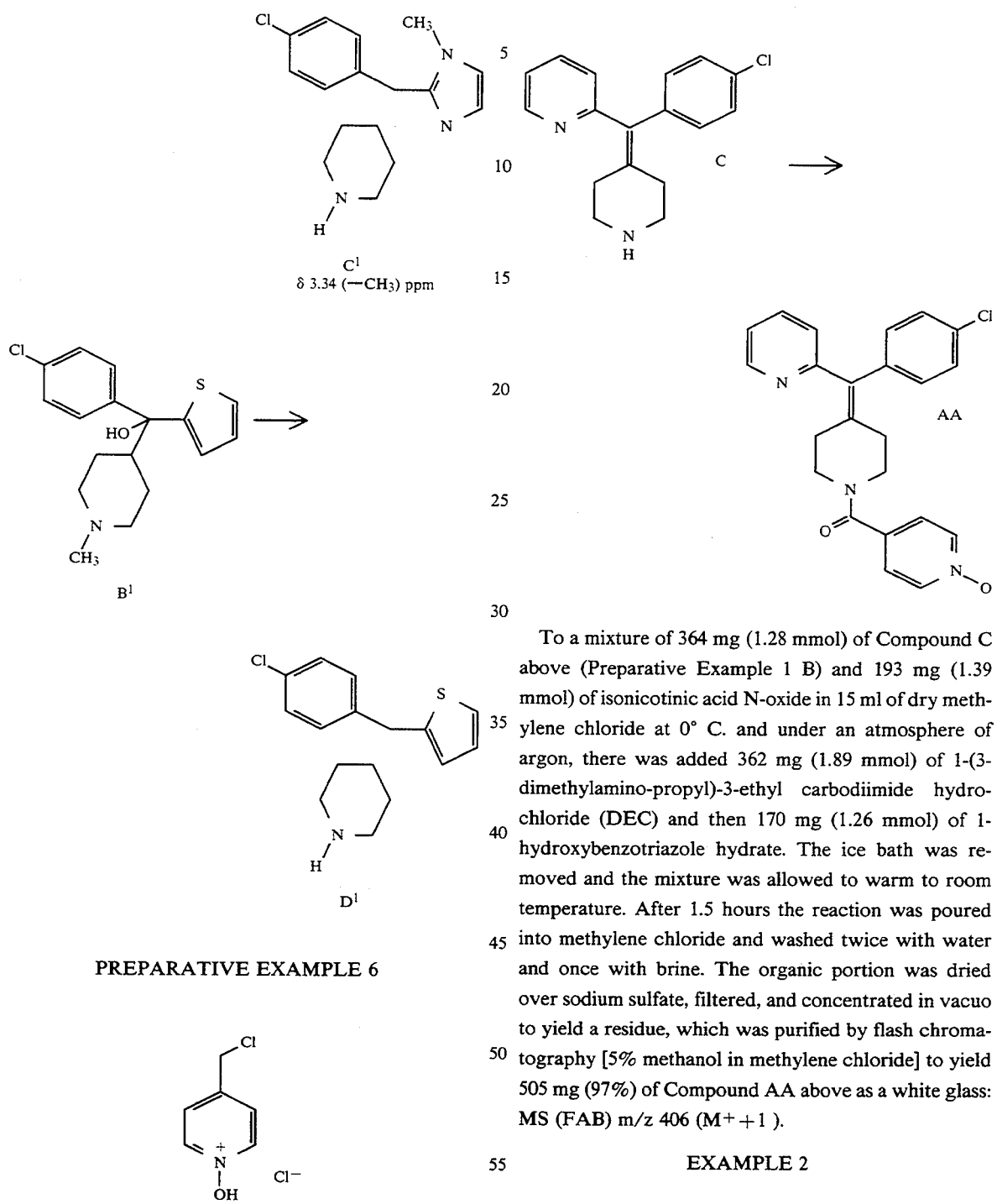

EXAMPLE 1

To a mixture of 364 mg (1.28 mmol) of Compound C above (Preparative Example 1 B) and 193 mg (1.39 mmol) of isonicotinic acid N-oxide in 15 ml of dry methylene chloride at 0° C. and under an atmosphere of argon, there was added 362 mg (1.89 mmol) of 1-(3-dimethylamino-propyl)-3-ethyl carbodiimide hydrochloride (DEC) and then 170 mg (1.26 mmol) of 1-hydroxybenzotriazole hydrate. The ice bath was removed and the mixture was allowed to warm to room temperature. After 1.5 hours the reaction was poured into methylene chloride and washed twice with water and once with brine. The organic portion was dried over sodium sulfate, filtered, and concentrated in vacuo to yield a residue, which was purified by flash chromatography [5% methanol in methylene chloride] to yield 505 mg (97%) of Compound AA above as a white glass: MS (FAB) m/z 406 (M++1 ).

EXAMPLE 2

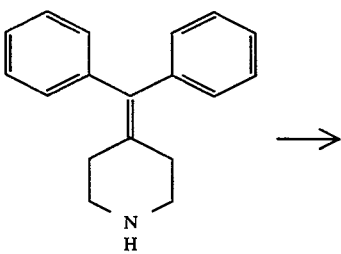

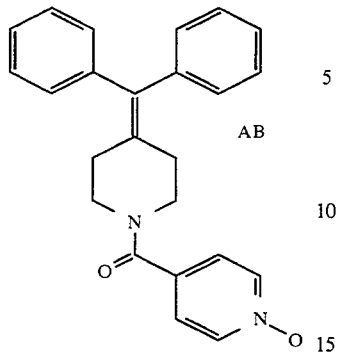

AB

To a mixture of 263 mg (1.05 mmol) of 4-(diphenylmethylene)piperidine [*Tetrahedron*, 44, 6197 (1988)] and 190 mg (1.37 mmol) of isonicotinic acid N-oxide in 15 ml of dry methylene chloride at 0° C. and under an atmosphere of argon there was added 300 mg (1.57 mmol) of DEC followed by 142 mg (1.05 mmol) of 1-hydroxybenzotriazole hydrate. The ice bath was removed and the mixture was allowed to warm to room temperature. After 1 hour the reaction was poured into methylene chloride and washed twice with water and once with brine. The organic portion was dried over sodium sulfate, filtered, and concentrated in vacuo to yield a residue, which was purified by flash chromatography [5% methanol in methylene chloride] to yield 353 mg (91%) of the title compound as an oil. It was further purified by recrystallization from methylene chloride /isopropyl ether to yield Compound AB above as a white solid: MP 151°-152° C.; MS (Cl) m/z 371 (M$^{30}$+1).

EXAMPLE 3

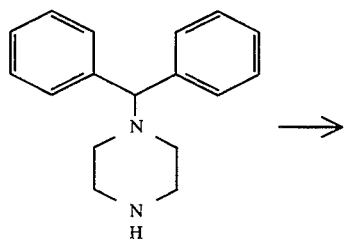

→

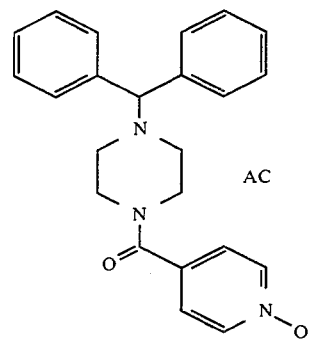

AC

Sch 47215

To a mixture of 2.01 g (8.04 mmol) of 1-diphenylmethylpiperazine, 1.11 g (7.98 mmol) of isonicotinic acid N-oxide, and 1.11 g (8.21 mmol) of 1-hydroxybenzotriazole hydrate in 40 ml of dry methylene chloride at 0° C. and under an atmosphere of nitrogen, there was added a solution of 1.62 g (10.2 mmol) of DEC in 40 ml of methylene chloride. The mixture was then slowly allowed to warm to room temperature. After 5 hours the reaction mixture was poured into 10% aqueous sodium dihydrogen phosphate (w/v) and extracted with methylene chloride. The organic portion was washed with brine, dried over magnesium sulfate, filtered, and concentrated in vacuo to yield a residue, which was purified by flash chromatography [5% methanol saturated with ammonia in methylene chloride] to yield the desired product. It was recrystallized from methylene chloride/ethyl acetate/isopropyl ether to afford 1.00 g (34%) of Compound AC above as a white solid: MP 168°-170° C.; MS (Cl) m/z 374 (M$^{30}$+1).

By employing basically the same procedure as set forth in EXAMPLE 3 above, but substituting the starting compounds of column 1 in Table 3 below for 1-diphenylmethylpiperazine, the compounds listed in column 2 in Table 3 were prepared. The physical data for these compounds of the invention are listed in column 3 of Table 3.

TABLE 3

| STARTING COMPOUND | COMPOUND OF THE INVENTION | PHYSICAL CHARACTERISTICS |
|---|---|---|
| | | glass; MS (Cl) m/z 408 (M$^+$ + 1) |

AD

TABLE 3-continued
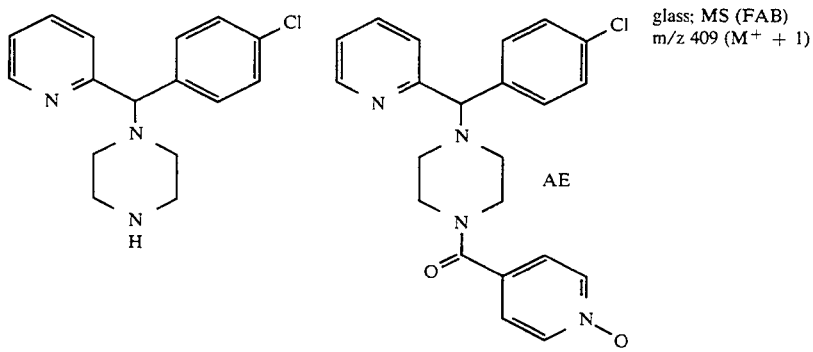
glass; MS (FAB)
m/z 409 (M+ + 1)
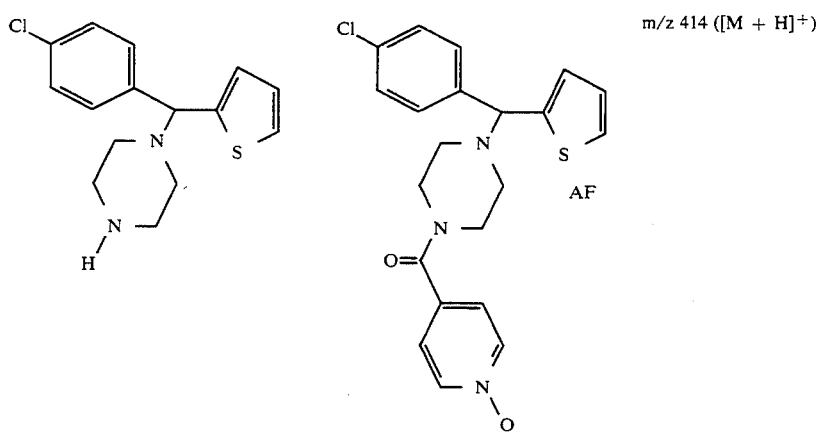
m/z 414 ([M + H]+)
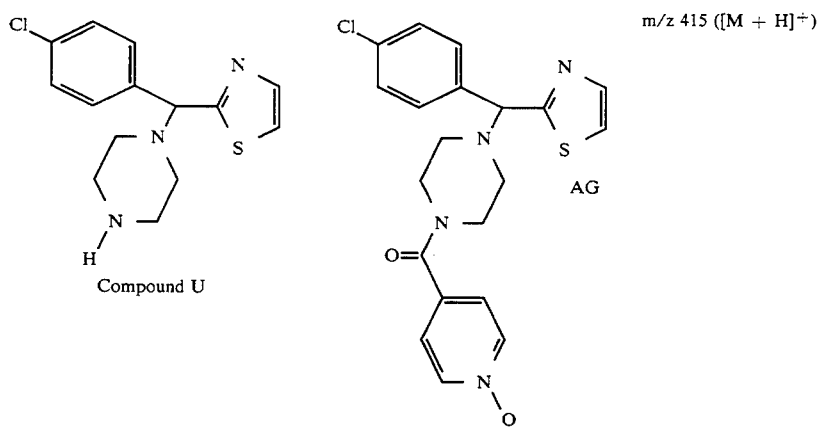
m/z 415 ([M + H]+)
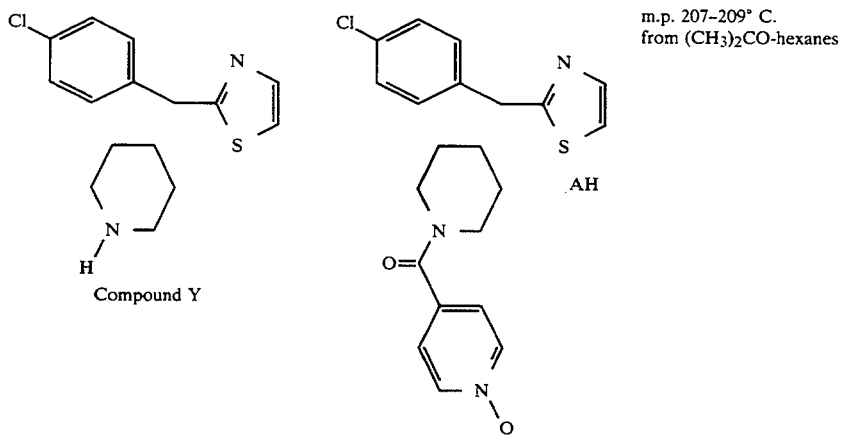
m.p. 207–209° C.
from (CH₃)₂CO-hexanes

TABLE 3-continued
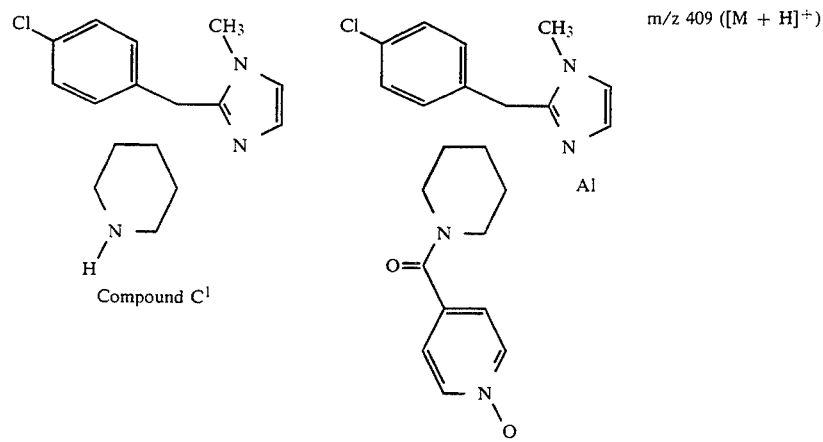
m/z 409 ([M + H]+)
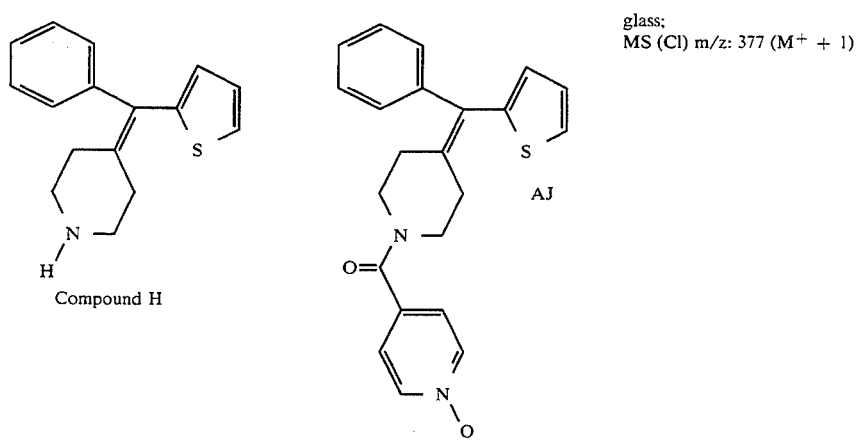
glass;
MS (CI) m/z: 377 (M+ + 1)
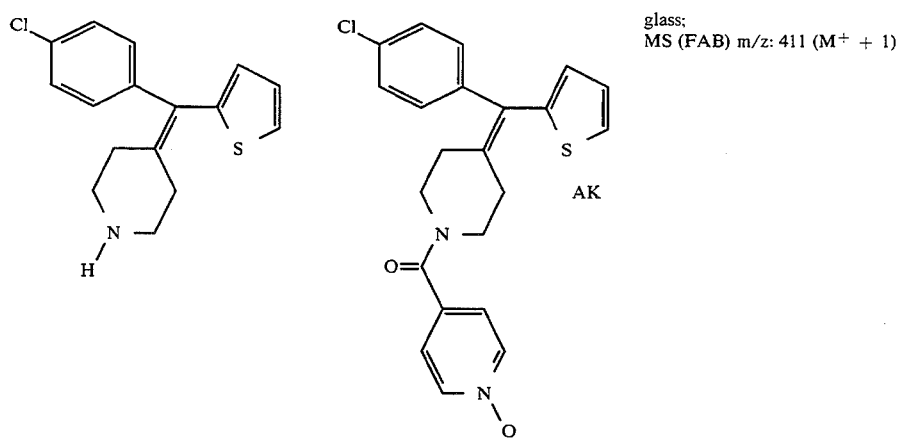
glass;
MS (FAB) m/z: 411 (M+ + 1)
EXAMPLE 4

TABLE 3-continued

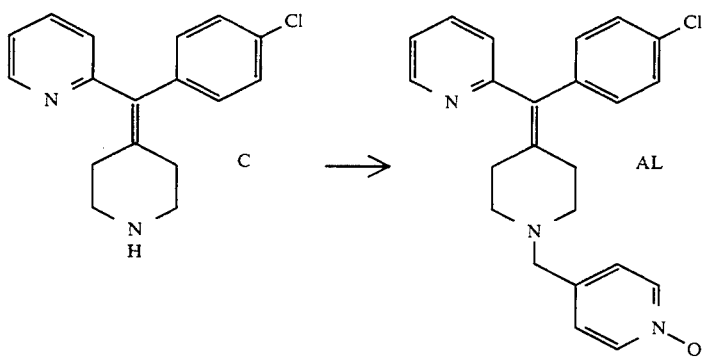

To a mixture of 129 mg (1.03 mmol) of 4-pyridylcarbinol N-oxide and 290 μl (2.06 mmol) of triethylamine in 10 ml of dry methylene chloride at 0° C. and under an atmosphere of nitrogen was added 80 μl (1.55 mmol) of methanesulfonyl chloride, followed after 25 minutes by another 40 μl (0.78 mmol) of methanesulfonyl chloride. After another 10 minutes the entire solution was transferred by syringe to a flask containing 292 mg (1.03 mmol) of Compound C above (Preparative Example 1B), 90 mg (1.04 mmol) of lithium bromide, and 140 mg (1.05 mmol) of lithium iodide. The mixture was refluxed for 5.5 hours, and was then poured into 1.0N aqueous sodium hydroxide and extracted three times with methylene chloride. The combined organic portions were dried over magnesium sulfate, filtered, and concentrated in vacuo. The isolated residue was then put through the entire process above in place of the 4-[(4-chlorophenyl) (2-pyridyl)methylene]piperidine. The mixture was then poured into 1.0N aqueous sodium hydroxide and extracted three times with methylene chloride. The combined organic portions were dried over magnesium sulfate, filtered, and concentrated in vacuo to provide an oil, which was purified twice by flash chromatography [6–8 % methanol saturated with ammonia in methylene chloride] to provide 118 mg (29%) of Compound AL above as a glass: MS (FAB) m/z 392 ($M^{30}+1$).

EXAMPLE 5

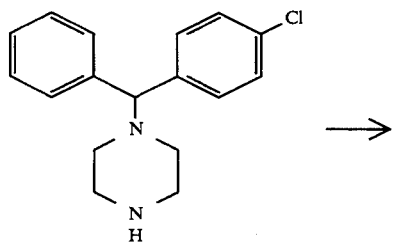

-continued

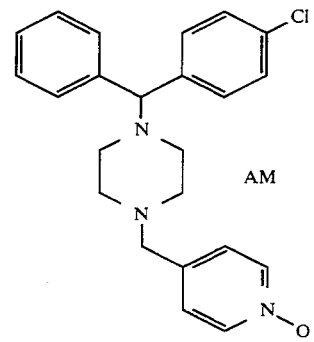

Methanesulfonyl chloride (790 μl, 10.2 mmol) was added over 25 minutes to a mixture of 871 mg (6.97 mmol) of 4-pyridylcarbinol N-oxide and 2.00 ml (10.5 mmol) of triethylamine in 60 ml of methylene chloride at 0° C. under an atmosphere of nitrogen. After another 10 minutes, 606 mg (6.98 mmol) of lithium bromide and then 2.00 g (7.00 mmol) of 1-[1-(4-chlorophenyl)benzyl]piperazine were added. The reaction mixture was refluxed for 4 hours, after which it was cooled, poured into 1.0N aqueous sodium hydroxide and extracted three times with methylene chloride. The combined organic extracts were washed with brine, dried over magnesium sulfate, filtered, and concentrated in vacuo to yield a residue which was purified three times by flash chromatography [2 to 5% methanol saturated with ammonia in methylene chloride] to provide 1.42 g (51%) of Compound AM above as a glass: MS (FAB) m/z 394 ($M^{30}+1$).

EXAMPLE 6

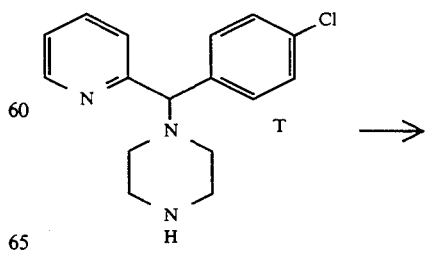

-continued

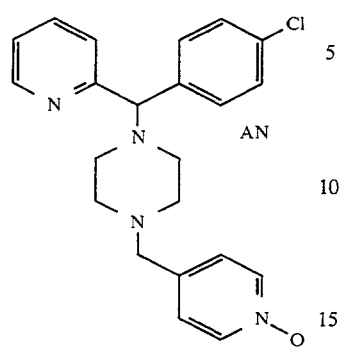

AN

Triphenyl phosphine (744 mg, 2.87 mmol) was added to a mixture containing 358 mg (2.87 mmol) of 4-pyridylcarbinol N-oxide and 951 mg (2.87 mmol) of carbon tetrabromide in 20 ml of dry methylene chloride at room temperature and under an atmosphere of nitrogen. After 45 minutes, a solution of 504 mg (1.75 mmol) of Compound T above (Preparative Example 3D) in 5 ml dry methylene chloride and then 400 µl (2.87 mmol) of triethylamine were added. After another 5.75 hours, the mixture was poured into 1.0N aqueous sodium hydroxide and extracted three times with methylene chloride. The combined organic extracts were dried over magnesium sulfate, filtered, and concentrated in vacuo to yield a residue, which was purified twice by flash chromatography [4% methanol saturated with ammonia/36% methylene chloride/60% acetonitrile; then 2 to 3% methanol saturated with ammonia in methylene chloride] to provide 289 mg (42%) of Compound AN above as a glass: MS (FAB) m/z 395 (M++1).

By employing basically the same procedure as outlined above but substituting Compound C 1 in place of Compound T, Compound AO below was prepared.

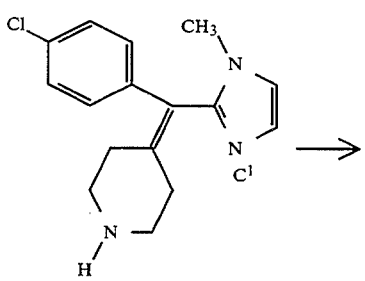

-continued

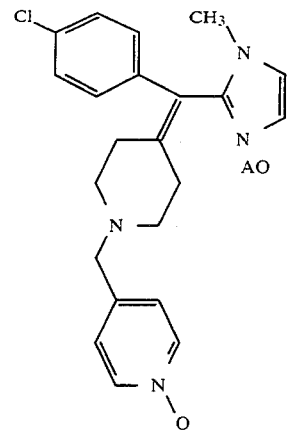

AO m/z 395 ([M + H]+)

EXAMPLE 7

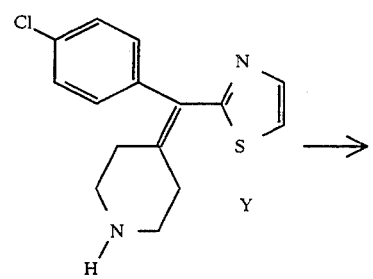

Y

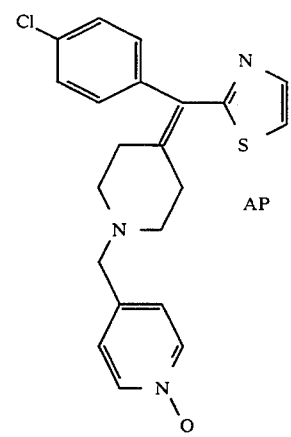

AP

A solution of compound Y above (0.26 g) in methanol (10 ml) was added to a cold (ice bath) solution of 4-(chloromethyl)-pyridine—N-oxide hydrochloride (0.22 g) and triethylamine (0.22 g)in methanol (10 ml). The reaction mixture was allowed to stir at 25° C. for 18 hrs. and was then concentrated to remove methanol. The residue was basified with concentrated aqueous ammonia and extracted with dichloromethane. The combined extracts were dried (MgSO4), filtered, and concentrated. Chromatography of the residue over silica gel and elution with methanol-dichloromethane (8%) under nitrogen pressure gave compound AP, m/z 398 ([M+H]+.

By employing basically the same procedure as set forth in EXAMPLE 7 above, but substituting the starting compounds in the lefthand column in Table 4 below for Compound C 1, the compounds listed in the center column in Table 4 were prepared. The physical data for these compounds of the invention are listed in the right-hand column of Table 4.

TABLE 4

| STARTING COMPOUND | COMPOUND OF THE INVENTION | PHYSICAL CHARACTERISTICS |
|---|---|---|
| (structure) | (structure) AQ | m/z 400 ([M + H]$^+$) |
| (structure) COMPOUND U | (structure) AR | m/z 401 ([M + H]$^+$) |

The following are examples of pharmaceutical dosage forms which contain a compound of the invention. As used therein, the term "active compound" is used to designate the compound

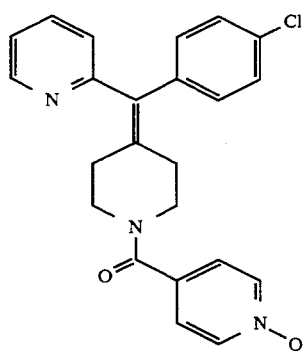

The scope of the invention in its pharmaceutical composition aspect is not to be limited by the examples provided, since any other compound of structural formula 1.0 can be substituted into the pharmaceutical composition examples.

Pharmaceutical Dosage Form Examples

EXAMPLE A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

| | Capsules | | |
|---|---|---|---|
| No. | Ingredient | mg/capsule | mg/capsule |
| 1. | Active compound | 100 | 500 |

| | Capsules | | |
|---|---|---|---|
| No. | Ingredient | mg/capsule | mg/capsule |
| 2. | Lactose USP | 106 | 123 |
| 3. | Corn Starch, Food Grade | 40 | 70 |
| 4. | Magnesium Stearate NF | 7 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by the structural formula 1.0:

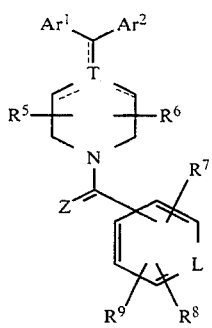

or a pharmaceutically acceptable salt or solvate thereof, wherein:

$Ar^1$ represents

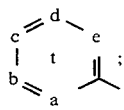

$Ar^2$ represents

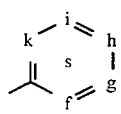

or a five-membered heterocyclic aromatic group selected from the group consisting of:

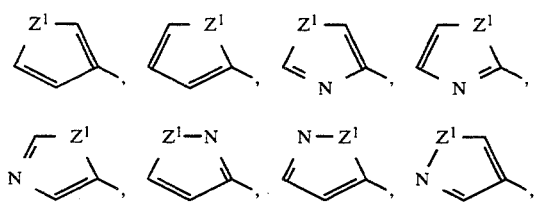

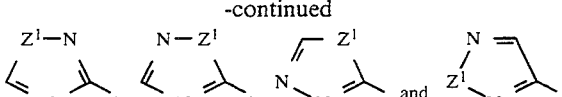

wherein $Z^1$ represents

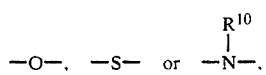

and wherein the substitutable carbon atoms of the five-membered heterocyclic group may optionally be substituted with a group $R^1$ as defined below;

one of a, b, c, d and e represents N or NO and the others represent CH or $CR^1$ or all of a, b, c, d and e represent CH or $CR^1$;

one of f, g, h, i and k represents N or NO and the others represent CH or $CR^2$ or all of f, g, h, i and k represent CH or $CR^2$;

L represents N or $N^+O^-$;

$R^1$ and $R^2$ may be the same or different and each $R^1$ and each $R^2$ independently represents halo, $-CF_3$, $-OR^{11}$, $-C(O)R^{11}$, $-SR^{11}$, $-S(O)_eR^{12}$ where e is 1 or 2, $-N(R^{11})_2$, $-NO_2$, $-OC(O)R^{11}$, $-CO_2R^{11}$, $-OCO_2R^{12}$, $-CON(R^{11})_2$, $-NR^{11}C(=O)R^{11}$, $-CN$, alkyl, aryl, alkenyl or alkynyl, which alkyl group may be substituted with $-OR^{11}$, $-SR^{11}$, $-N(R^{11})_2$ or $-CO_2R^{11}$ and which alkenyl group may be substituted with halo, $-OR^{12}$ or $-CO_2R^{11}$;

$R^5$ and $R^6$ may be the same or different and each independently represents H, alkyl or aryl, which alkyl may be substituted with $-OR^{11}$, $-SR^{11}$ or $-N(R^{11})_2$;

in addition, $R^5$ and $R^6$ together on the same carbon atom may represent $=O$ or $=S$;

each of $R^7$, $R^8$ and $R^9$ independently represents H, halo, $-CF_3$, $-OR^{11}$, $-C(O)R^{11}$, $SR^{11}$, $-S(O)_eR^{12}$ where e is 1 or 2, $-N(R^{11})_2$, $-NO^2$, aryl, alkenyl or alkynyl, which alkyl group may be substituted with $-OR^{11}$, $-SR^{11}$, $-N(R^{11})_2$, or $-CO_2R^{11}$ and which alkenyl group may be substituted with halo, $-OR^{12}$ or $-CO_2R^{11}$;

$R^{10}$ represents H or alkyl;

each $R^{11}$ independently represents H, alkyl or aryl;

each $R^{12}$ independently represents alkyl or aryl;

T represents CH, C or N, with the dotted lines attached to T representing one double bond in one of the indicated positions when T is C and being absent when T is CH or N; and Z represents O or S; and with the proviso that when Z is O, and T is C or CH, and $Ar^1$ is ring t wherein all of a, b, c, d, and e represent CH, and $Ar^2$ is ring s wherein all of f, g, h, i, and k represent CH, then L represents $N^+O^-$; and wherein said alkyl contains from one to twenty carbon atoms; said alkenyl contains from 2 to 12 carbon atoms; said alkynyl contains from 2 to 12 carbon atoms; and said aryl represents a carbocyclic group containing from 6 to 14 carbon atoms.

2. A compound according to claim 1 of the formula 1.1:

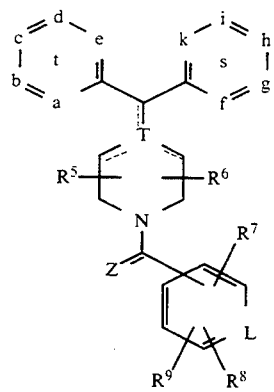

1.1 wherein a, b, c, d, e, f, g, h, i, k, T, Z, L, $R^5$, $R^6$, $R^7$, $R^8$, $R^9$ and the dotted lines are as defined in claim 1.

3. A compound according to claim 1 of the formula 1.3:

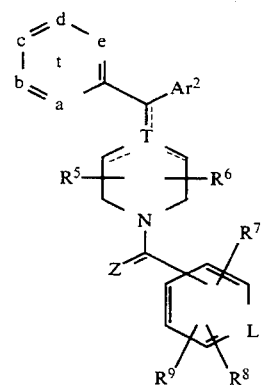

1.3 wherein a, b, c, d, e, T, Z, L, $R^5$, $R^6$, $R^7$, $R^8$, $R^9$ and the dotted lines are as defined in claim 1 and $Ar^2$ represents a five-membered heterocyclic group selected from:

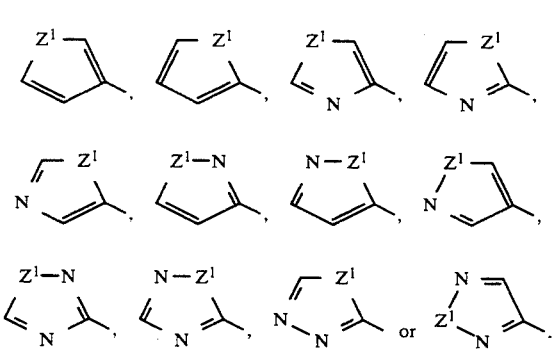

where $Z^1$ represents

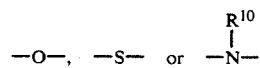

and $R^{10}$ is defined as in claim 1.

4. A compound according to claim 1 of the formula 1.4:

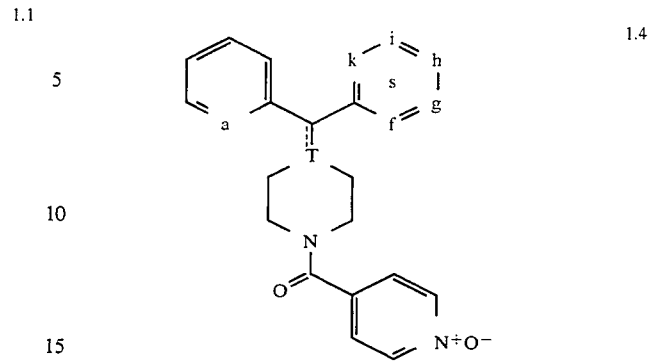

1.4 wherein f, g, h, i, k, T and the dotted lines are as defined in claim 1 and a is N or CH.

5. A compound according to claim 1 of the formula 1.6:

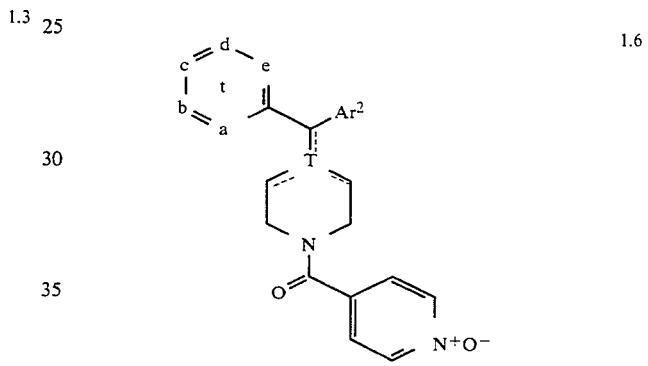

1.6 wherein a, b, c, d, e, T and the dotted lines are as defined in claim 1 and $Ar^2$ is selected from:

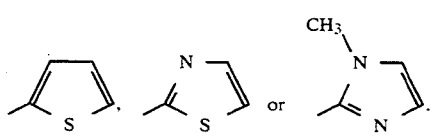

6. A compound according to claim 1 selected from:

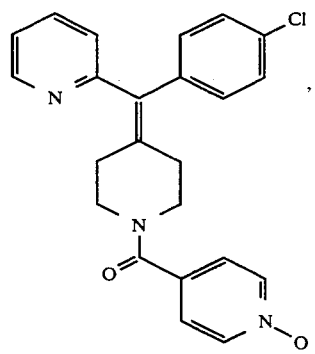

-continued
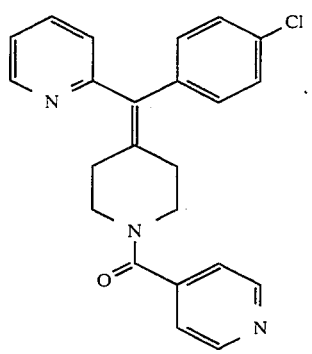
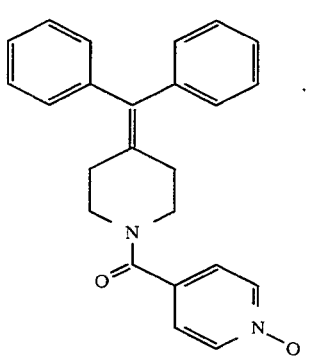
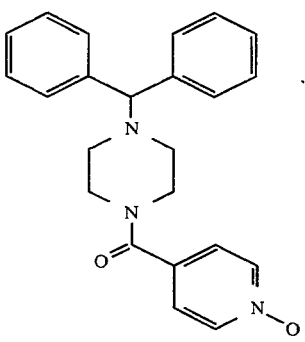
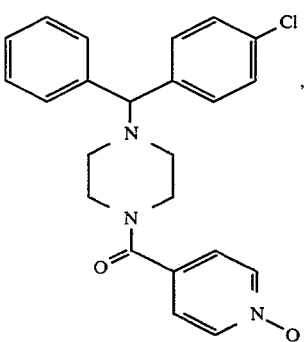
-continued
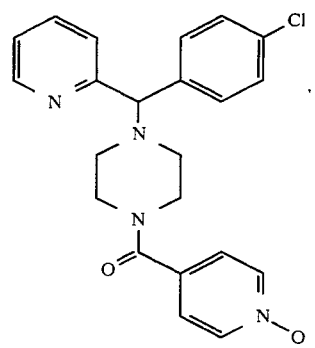
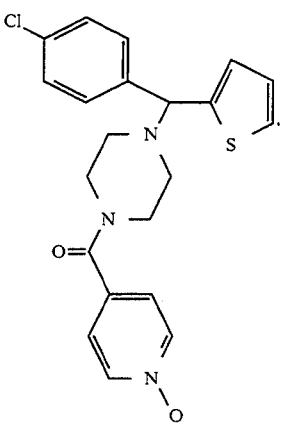
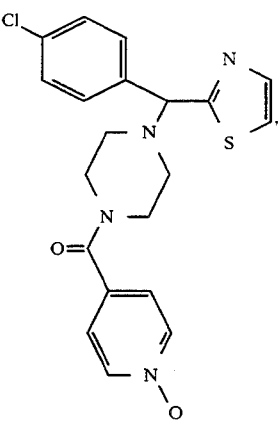
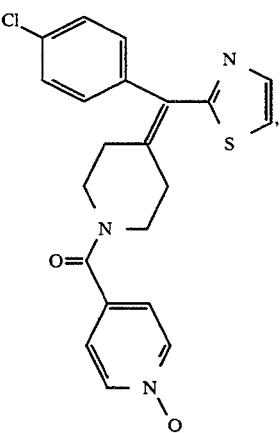

-continued

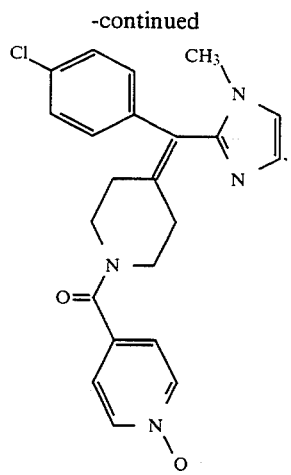

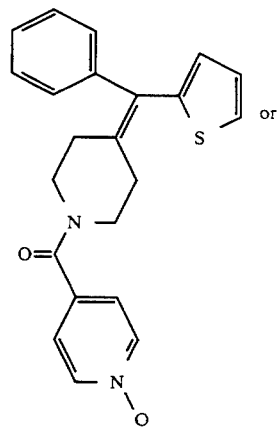 or

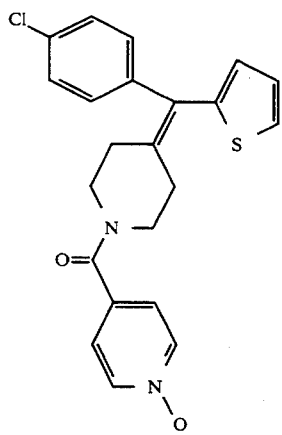

or a pharmaceutically acceptable salt of such a compound.

7. A pharmaceutical composition comprising an effective amount a compound according to claim 1 in combination with a pharmaceutically acceptable carrier.

8. A method for treating allergic reaction or inflammation in a mammal comprising administering to the mammal an effective amount of a compound of claim 1 for such purpose.

9. The compound of claim 1 represented by the structural formula 1.0:

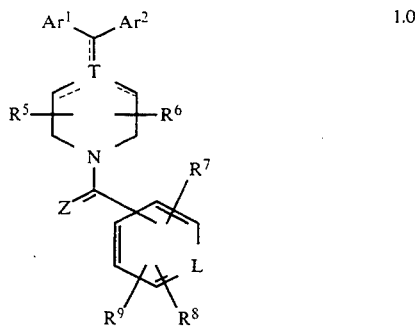

or a pharmaceutically acceptable salt or solvate thereof, wherein:

$Ar^1$ represents

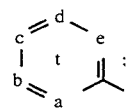

$Ar^2$ represents

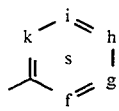

or a five-membered heterocyclic aromatic group selected from the group consisting of:

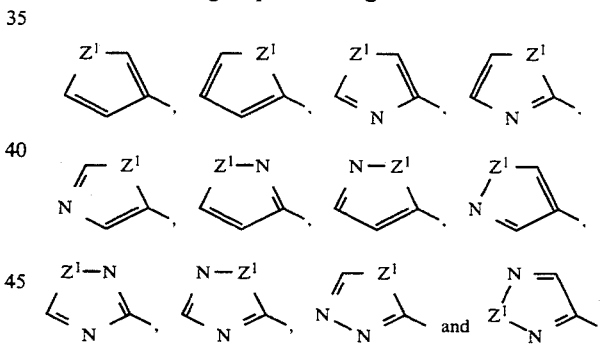

wherein $Z^1$ represents

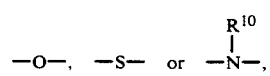

and wherein the substitutable carbon atoms of the five-membered heterocyclic group may optionally be substituted with a group $R^1$ as defined below;
one of a, b, c, d and e represents N or NO and the others represent CH or $CR^1$ or all of a, b, c, d and e represent CH or $CR^1$;
one of f, g, h, i and k represents N or NO and the others represent CH or $CR^2$ or all of f, g, h, i and k represent CH or $CR^2$;
L represents $N^+O^-$;
$R^1$ and $R^2$ may be the same or different and each $R^1$ and each $R^2$ independently represents halo, $-CF_3$, $-OR^{11}$, $-C(O)R^{11}$, $-SR^{11}$, $-S(O)_eR^{12}$ where e is 1 or 2, $-N(R^{11})_2$, $-NO_2$, $-OC(O)R^{11}$, $-CO_2R^{11}$, —OCO$_2$R$^{12}$, —CON(R$^{11}$)$_2$, —NR$^{11}$C(=O)R$^{11}$, —CN, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halo, —OR$^{12}$ or —CO$_2$R$^{11}$;

R$^5$ and R$^6$ may be the same or different and each independently represents H, alkyl or aryl, which alkyl may be substituted with —OR$^{11}$, —SR$^{11}$ or —N(R$^{11}$)$_2$;

in addition, R$^5$ and R$^6$ together on the same carbon atom may represent =O or =S;

each of R$^7$, R$^8$ and R$^9$ independently represents H, halo, —CF$_3$, —OR$^{11}$, —C(O)R$^{11}$, SR$^{11}$, —S(O)$_e$R$^{12}$ where e is 1 or 2, —N(R$^{11}$)$_2$, —NO$_2$, —CN, —CO$_2$R$^{11}$, —OCO$_2$R$^{12}$, —OC(O)R$^{11}$, —CON(R$^{11}$)$_2$, —NR$^{11}$C(O)R$^{11}$, alkyl, aryl, alkenyl or alkynyl, which alkyl group may be substituted with —OR$^{11}$, —SR$^{11}$, —N(R$^{11}$)$_2$, or —CO$_2$R$^{11}$ and which alkenyl group may be substituted with halo, —OR$^{12}$ or —CO$_2$R$^{11}$;

R$^{10}$ represents H or alkyl;

each R$^{11}$ independently represents H, alkyl or aryl;

each R$^{12}$ independently represents alkyl or aryl;

T represents CH, C or N, with the dotted lines attached to T representing one double bond in one of the indicated positions when T is C and being absent when T is CH or N;

Z represents O; and wherein said alkyl contains from one to twenty carbon atoms; said alkenyl contains from 2 to 12 carbon atoms; said alkynyl contains from 2 to carbon atoms; and said aryl represents a carbocyclic group containing from 6 to 14 carbon atoms.

10. The compound of claim 1 represented by the structural formula 1.0:

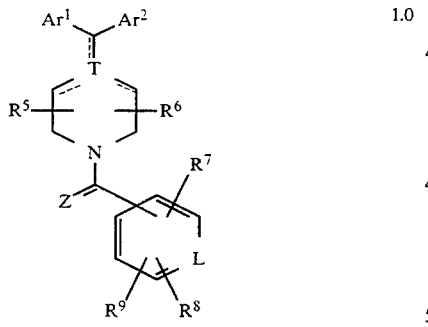

1.0 or a pharmaceutically acceptable salt or solvate thereof, wherein:

Ar$^1$ represents

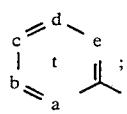

Ar$^2$ represents

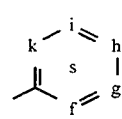

or a five-membered heterocyclic aromatic group selected from the group consisting of:

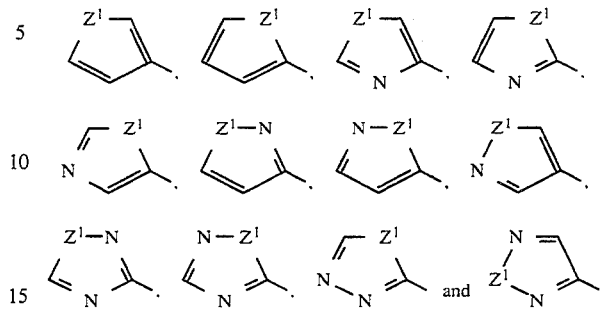

wherein Z$^1$ represents

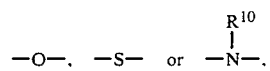

and wherein the substitutable carbon atoms of the five-membered heterocyclic group may optionally be substituted with a group R$^1$ as defined below;

when T represents C or CH, then one of a, b, c, d and e represents N or NO and the others represent CH or CR$^1$;

when T represents N, then one of a, b, c, d and e represents N or NO and the others represent CH or CR$^1$ or all of a, b, c, d and e represent CH or CR$^1$;

one of f, g, h, i and k represents N or NO and the others represent CH or CR$^2$ or all of f, g, h, i and k represent CH or CR$^2$;

L represents N;

R$^1$ and R$^2$ may be the same or different and each R$^1$ and each R$^2$ independently represents halo, —CF$_3$, —OR$^{11}$, —C(O)R$^{11}$, —SR$^{11}$, —S(O)$_e$R$^{12}$ where e is 1 or 2, —N(R$^{11}$)$_2$, —NO$_2$, —OC(O)R$^{11}$, —CO$_2$R$^{11}$, —OCO$_2$R$^{12}$, —CON(R$^{11}$)$_2$, —NR$^{11}$C(=O)R$^{11}$, —CN, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halo, —OR$^{12}$ or —CO$_2$R$^{11}$;

R$^5$ and R$^6$ may be the same or different and each independently represents H, alkyl or aryl, which alkyl may be substituted with —OR$^{11}$, —SR$^{11}$ or —N(R$^{11}$)$_2$;

in addition, R$^5$ and R$^6$ together on the same carbon atom may represent =O or =S;

each of R$^7$, R$^8$ and R$^9$ independently represents H, halo, —CF$_3$, —OR$^{11}$, —C(O)R$^{11}$, SR$^{11}$, —S(O)$_e$R$^{12}$ where e is 1 or 2, —N(R$^{11}$)$_2$, —NO$_2$, —CN, —CO$_2$R$^{11}$, —OCO$_2$R$^{12}$, —OC(O)R$^{11}$, —CON(R$^{11}$)$_2$, —NR$^{11}$C(O)R$^{11}$, alkyl, aryl, alkenyl or alkynyl, which alkyl group may be substituted with —OR$^{11}$, —SR$^{11}$, —N(R$^{11}$)$_2$, or —CO$_2$R$^{11}$ and which alkenyl group may be substituted with halo, —OR$^{12}$ or —CO$_2$R$^{11}$;

R$^{10}$ represents H or alkyl;

each R$^{11}$ independently represents H, alkyl or aryl;

each R$^{12}$ independently represents alkyl or aryl;

T represents CH, C or N, with the dotted lines attached to T representing one double bond in one of the indicated positions when T is C and being absent when T is CH or N;

Z represents O; and wherein said alkyl contains from one to twenty carbon atoms; said alkenyl contains from 2 to 12 carbon atoms; said alkynyl contains from 2 to 12 carbon atoms; and said aryl represents a carbocyclic group containing from 6 to 14 carbon atoms.

11. The compound of claim 1 represented by the structural formula 1.0:

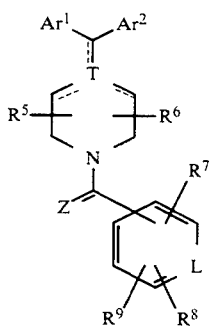
1.0 or a pharmaceutically acceptable salt or solvate thereof, wherein:

Ar$^1$ represents

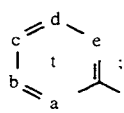

Ar$^2$ represents

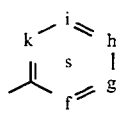

or a five-membered heterocyclic aromatic group selected from the group consisting of:

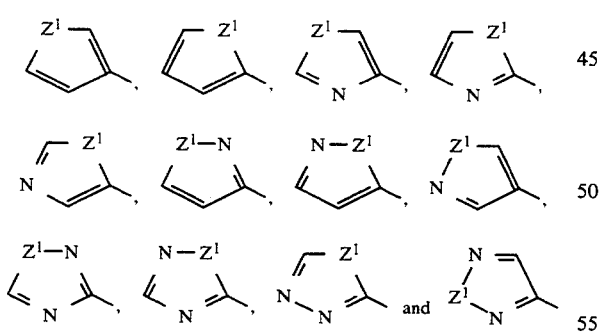

wherein Z$^1$ represents

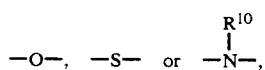

and wherein the substitutable carbon atoms of the five-membered heterocyclic group may optionally be substituted with a group R$^1$ as defined below;

one of a, b, c, d and e represents N or NO and the others represent CH or CR$^1$ or all of a, b, c, d and e represent CH or CR$^1$;

one of f, g, h, i and k represents N or NO and the others represent CH or CR$^2$ or all of f, g, h, i and k represent CH or CR$^2$;

L represents N or N$^+$O$^-$;

R$^1$ and R$^2$ may be the same or different and each R$^1$ and each R$^2$ independently represents halo, —CF$_3$, —OR$^{11}$, —C(O)R$^{11}$, —SR$^{11}$, —S(O)$_e$R$^{12}$ where e is 1 or 2, —N(R$^{11}$)$_2$, —NO$_2$, —OC(O)R$^{11}$, —CO$_2$R$^{11}$, —OCO$_2$R$^{12}$, —CON(R$^{11}$)$_2$, —NR$^{11}$C(=O)R$^{11}$, —CN, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halo, —OR$^{12}$ or —CO$_2$R$^{11}$;

R$^5$ and R$^6$ may be the same or different and each independently represents H, alkyl or aryl, which alkyl may be substituted with —OR$^{11}$, —SR$^{11}$ or —N(R$^{11}$)$_2$;

in addition, R$^5$ and R$^6$ together on the same carbon atom may represent =O or =S;

each of R$^7$, R$^8$ and R$^9$ independently represents H, halo, —CF$_3$, —OR$^{11}$, —C(O)R$^{11}$, SR$^{11}$, —S(O)$_e$R$^{12}$ where e is 1 or 2, —N(R$^{11}$)$_2$, —NO$_2$, —CN, —CO$_2$R$^{11}$, —OCO$_2$R$^{12}$, —OC(O)R$^{11}$, —CON(R$^{11}$)$_2$, —NR$^{11}$C(O)R$^{11}$, alkyl, aryl, alkenyl or alkynyl, which alkyl group may be substituted with —OR$^{11}$, —SR$^{11}$, —N(R$^{11}$)$_2$, or —CO$_2$R$^{11}$ and which alkenyl group may be substituted with halo, —OR$^{12}$ or —CO$_2$R$^{11}$;

R$^{10}$ represents H or alkyl;

each R$^{11}$ independently represents H, alkyl or aryl;

each R$^{12}$ independently represents alkyl or aryl;

T represents CH, C or N, with the dotted lines attached to T representing one double bond in one of the indicated positions when T is C and being absent when T is CH or N;

Z represents S; and wherein said alkyl contains from one to twenty carbon atoms; said alkenyl contains from 2 to 12 carbon atoms; said alkynyl contains from 2 to carbon atoms; and said aryl represents a carbocyclic group containing from 6 to 14 carbon atoms.

12. The compound of claim 9 having the formula:

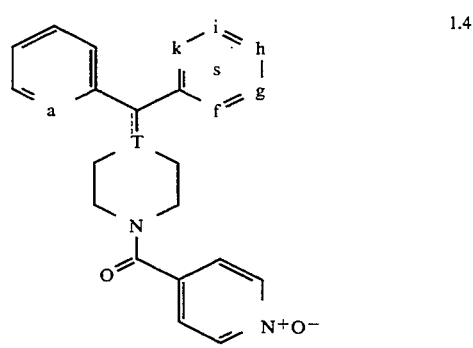
1.4 wherein a is N or CH and T is C or N.

13. The compound of claim 9 having the formula:

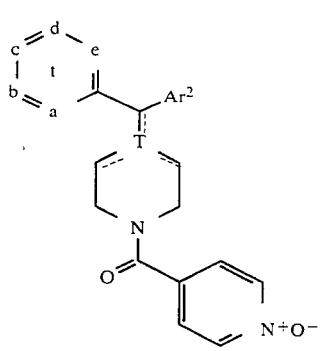
wherein T is C or N and Ar² is selected from:
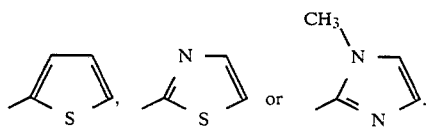
14. The compound of claim 6 selected from:
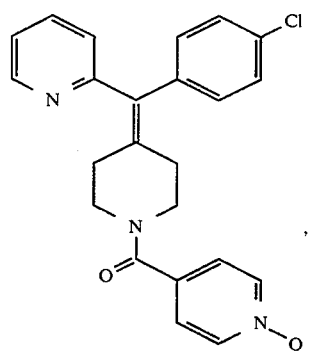
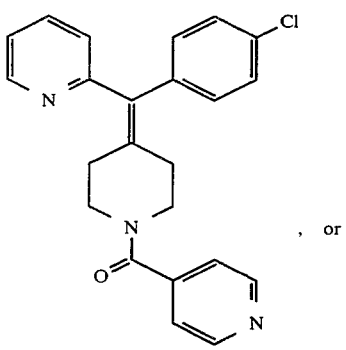
, or
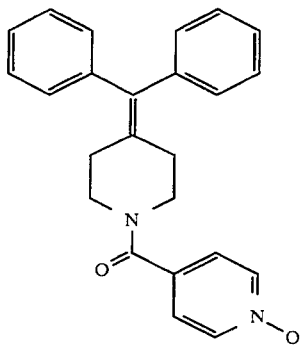
or a pharmaceutically acceptable salt of such a compound.
15. The compound of claim 6 selected from:
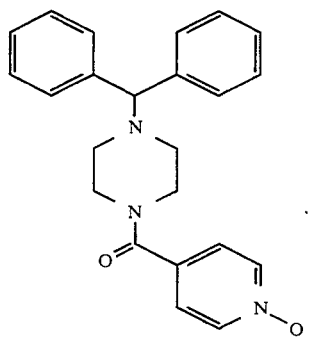
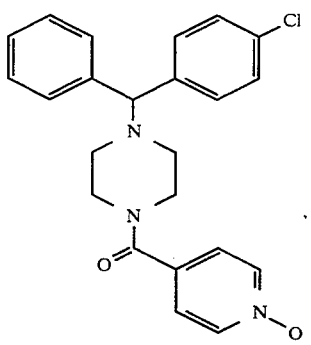
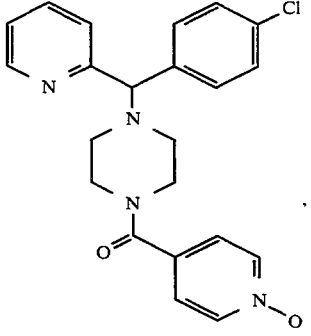

-continued
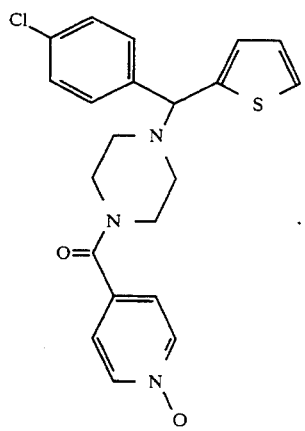
, or
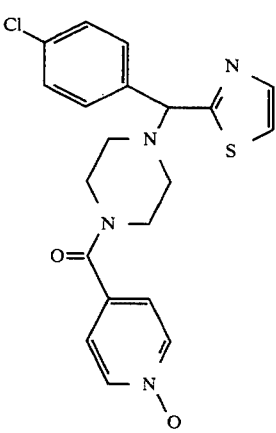
or a pharmaceutically acceptable salt of such a compound.
16. The compound of claim 6 selected from:
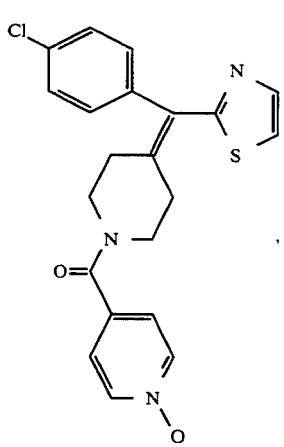
-continued
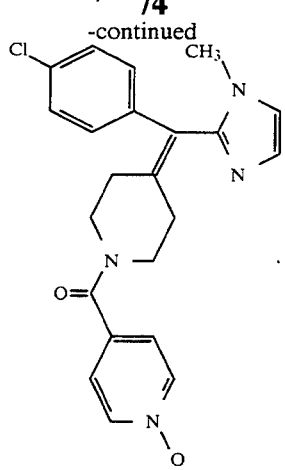
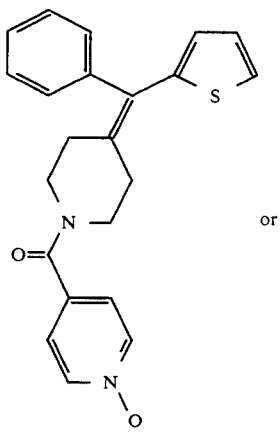
or
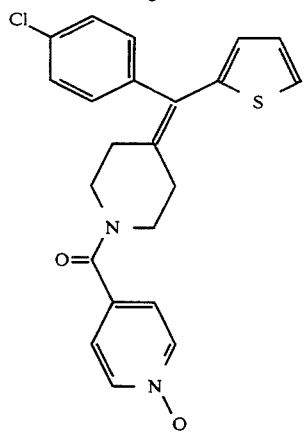
or a pharmaceutically acceptable salt of such a compound.
17. The compound of claim 15 having the formula:
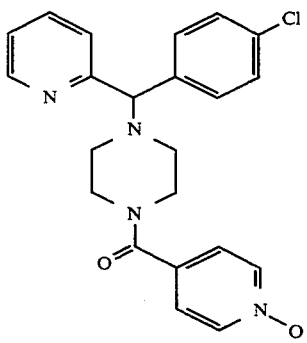
or a pharmaceutically acceptable salt of such a compound.
* * * * *